United States Patent
Viggiano et al.

(10) Patent No.: US 10,723,857 B1
(45) Date of Patent: Jul. 28, 2020

(54) POLYIMIDE AEROGELS WITH REDUCED SHRINKAGE FROM ISOTHERMAL AGING

(71) Applicant: U. S. A., as represented by the Administrator of the National Aeronautics and Space Administration, Washington, DC (US)

(72) Inventors: Rocco P. Viggiano, Elyria, OH (US); Mary Ann B. Meador, Strongsville, OH (US)

(73) Assignee: United States of America as Represented by the Administrator of National Aeronautics and Space Administration, Washington, DC (US)

(*) Notice: Subject to any disclaimer, the term of this patent is extended or adjusted under 35 U.S.C. 154(b) by 0 days.

(21) Appl. No.: 15/486,732

(22) Filed: Apr. 13, 2017

Related U.S. Application Data

(60) Provisional application No. 62/323,126, filed on Apr. 15, 2016.

(51) Int. Cl.
*C08J 9/00* (2006.01)
*C08G 73/10* (2006.01)
*C08J 9/28* (2006.01)

(52) U.S. Cl.
CPC ............ *C08J 9/28* (2013.01); *C08G 73/1067* (2013.01); *C08J 2201/026* (2013.01); *C08J 2201/0502* (2013.01); *C08J 2205/026* (2013.01); *C08J 2379/08* (2013.01)

(58) Field of Classification Search
CPC .. C08J 2205/026; C08J 9/28; C08J 2201/026; C08G 73/1067
See application file for complete search history.

(56) References Cited

U.S. PATENT DOCUMENTS 9,109,088 B2 * 8/2015 Meador ............... C08G 73/101

OTHER PUBLICATIONS

Kim et al., "Synthesis and Characterization of Highly Soluble and Oxygen Permeable new Polyimides Based on Twisted Biphenyl Dianhydride and Spirofluorene Diamine," Macromolecules (2005), 38, pp. 7950-7956. (Year: 2005).*
Mary Ann Meador, Polyimide Aerogels with Amide Cross-Links: A Low Cost Alternativefor Mechanically Strong Polymer Aerogels, American Chemical Society Applied Matereial & Interfaces, 2015, 1240-1249, 7.

* cited by examiner

*Primary Examiner* — Kara B Boyle
(74) *Attorney, Agent, or Firm* — Robert H. Earp, III; Helen M. Galus

(57) ABSTRACT

A polyimide aerogel and method of making the aerogel is disclosed. The polymer backbone of the aerogel includes a cardo-diamine. The disclosed polyimide aerogel is less susceptible to temperature induced shrinkage than a polyimide aerogel that does not include a cardo-diamine.

6 Claims, 18 Drawing Sheets b) 0.123 g/cm³, 20.7% Shrinkage a) 0.141 g/cm$^3$, 360 m$^2$/g, 92.0% porous b) 0.0629 g/cm$^3$, 439 m$^2$/g, 96.4% porous a) 0.386 g/cm³, 29.9% Shrinkage b) 0.123 g/cm³, 20.7% Shrinkage

POLYIMIDE AEROGELS WITH REDUCED SHRINKAGE FROM ISOTHERMAL AGING

CROSS-REFERENCE TO RELATED APPLICATIONS

This application claims the benefit of U.S. Provisional Patent Application Ser. No. 62/323,136 entitled "Polyimide Aerogels with Reduced Shrinkage from Isothermal Aging" filed on Apr. 15, 2016. The entirety of the above-noted application is incorporated by reference herein.

ORIGIN OF THE INVENTION

The invention described herein was made by employees of the United States Government and may be manufactured and used by or for the Government for Government purposes without the payment of any royalties thereon or therefor.

BACKGROUND

Aerogels are porous solids with high surface areas that are made by forming a gel network and removing the solvent without causing pore collapse. Due to characteristics such as high surface area, high porosity, and low density, these lightweight aerogels are attractive for use as thermal insulators, low dielectric substrates, catalyst supports, and as building and construction materials.

The most common class of aerogels is silica aerogels. Silica aerogels are extremely fragile and moisture sensitive. As a result, the utility of monolithic silica aerogels is limited to a few exotic applications such as thermal insulation to protect the Warm Electronics Boxes (WEB) onboard the Mars Exploration Rovers from the extreme temperatures present in the Martian environment for an extended period of time. Silica aerogels were also implemented in the aerogel collection grid, a panel comprised of an array of silica aerogel, deployed as a part of the Stardust spacecraft in January 2004. Polyimide aerogels are a relatively new category of aerogels which possess superior mechanical properties to the silica aerogels. However, in their current form, polyimide aerogels undergo dramatic thermally induced shrinkage at temperatures of just 150° C. Shrinkage results in densification of the aerogel as well as a change in pore size and shape which negatively impacts its insulation characteristics. Shrinkage reduces porosity and increases density, thus, increasing thermal conductivity. This drastically limits the scope of the use of polyimide aerogels, especially in scenarios where the insulation would experience elevated temperatures for extended periods of time.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

Polymer aerogels have become a major research focus in the field of aerogels. With unique advantages over inorganic aerogels including higher strengths and compressive moduli, greater toughness, and the ability to be fabricated as a flexible thin film; polymer aerogels have supplanted inorganic aerogels in numerous applications. Of the many polymer aerogels presently available, polyimide aerogels have a distinction for possessing high thermal stability as well as excellent mechanical properties. Research on this class of polymer aerogels has shown that while the onset of thermal decomposition for these materials is typically very high (greater than 500° C.), the aerogels will undergo dramatic thermally induced shrinkage at temperatures well below their glass transition temperature (Tg) or their decomposition temperature. This severely limits the types of applications for polyimide aerogels.

The innovation is a polyimide aerogel comprising a rigid cardo-diamine moiety in the polymer chain. These rigidified polymer chains are cross-linked to create a network structure that gels in solution. The gel can then be dried into an aerogel.

In one aspect of the innovation, the incorporation of a bulky, space-filling moiety into the polymer backbone reduces thermal shrinkage in a polyimide aerogel. Bulky groups are considered to be sterically hindering which can disrupt certain chemical reactions as well as rotation about chemical bonds. Other bulky moieties include, but are not limited to: adamantyl, triptycene, cardo-phenolphthalein (PPH), an imide of cardo-phenolphthalein (PPH), cardo-anthrone, cardo-fluorene, cardo-norbornane, and cardo-cyclohexane groups. Chemical structures for examples of acceptable bulky moieties include:

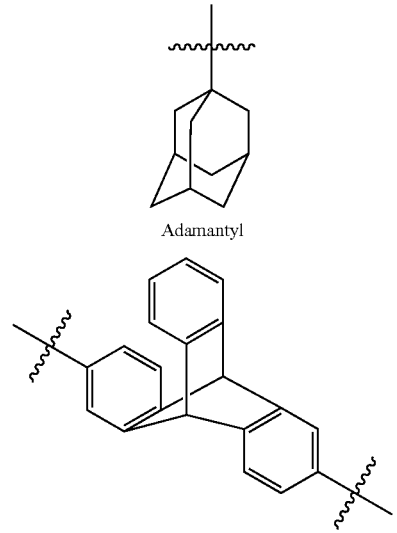

Adamantyl

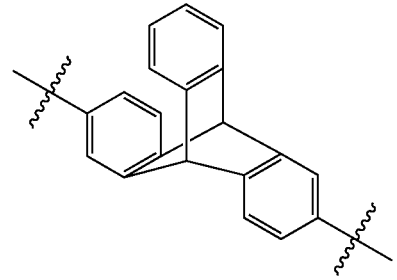

Triptycene

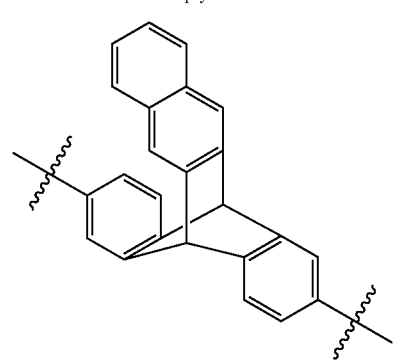

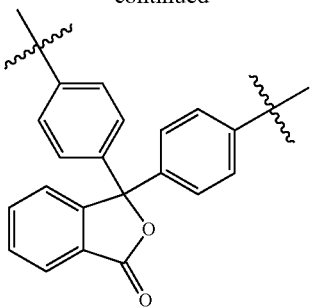

Cardo-Phenolphthalein

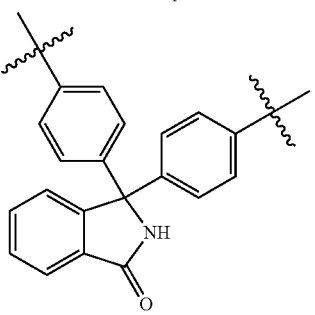

Imide of Cardo-Phenolphthalein

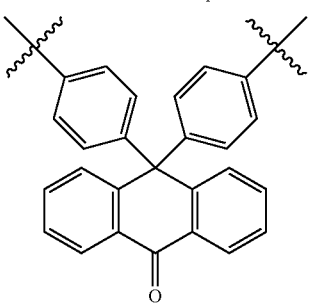

Cardo-Anthrone

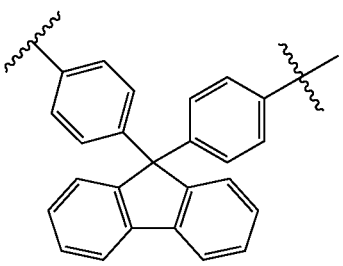

Cardo-Fluorene

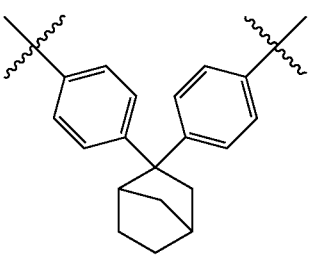

Cardo-Norbornane

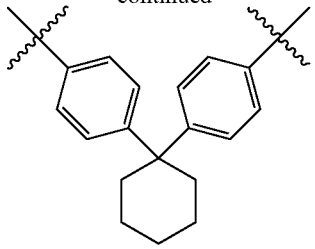

Cardo-Cyclohexane

In one embodiment, the bulky, space-filling moiety is 9,9'-bis(4-aminophenyl)fluorene (BAPF). The resulting polyimide aerogels showed a reduction in thermally induced shrinkage by as much as 50% compared to polyimide aerogels that do not contain BAPF.

In one aspect of the innovation, the polyimide aerogel has reduced temperature induced shrinkage. The polyimide aerogel comprises an oligomer backbone with n repeating units. In one embodiment, n is at least 10. In another embodiment, n is in the range of about 20 to about 40 repeating units. In yet another embodiment, n is at least 30.

In an aspect of the innovation, the oligomer backbone includes a cardo-diamine. In one embodiment, the cardo-diamine includes a bulky fluorene moiety. Suitable cardo-diamine moieties include anthrone, phenolphthalein (PPH), imide version of phenolphthalein (PPH), norbornane, cyclohexane, or a combination of two or more thereof. In one embodiment, the cardo-diamine is 9,9'-bis(4-aminophenyl)fluorene (BAPF).

In one embodiment, the cardo-diamine comprises at least about 10 mol %; at least about 20 mol %; at least about 30 mol %; at least about 40 mol %; at least about 50 mol %; at least about 60 mol %; or even at least about 70 mol % of the backbone.

In another embodiment, the polymer concentration is at least about 5 wt %, at least 6 wt %, at least about 7 wt %, at least about 8 wt %, at least about 9 wt %, at least about 10 wt %, at least about 11 wt %, at least about 12 wt %, at least about 13 wt %, at least about 14 wt %, or at least 15 wt %. In another embodiment, the polymer concentration is in the range of about 5 wt % to about 20 wt %; about 5 wt % to about 15 wt %, or about 5 wt % to about 10 wt %. In one embodiment, the polymer concentration is in the range of about 7 wt % to about 15 wt % or from about 7 wt % to about 10 wt %.

The repeating unit may comprise at least one diamine and one dianhydride. In one embodiment, the diamine is selected from the group consisting of 2,2'-bis[4-(4-aminophenoxy)phenyl]propane (BAPP), 3,4'-oxydianiline (3,4'-ODA), 4,4'-oxydianiline (4,4'-ODA), p-phenylene diamine (PPDA), 2,2'-dimethylbenzidine (DMBZ), bisaniline-p-xylidene (BAX), 4,4'-bis(4-aminophenoxy)biphenyl (4,4'-BAPB), 3,3'-bis(4-aminophenoxy)biphenyl (3,3'-BAPB), 4,4'-(1,4-phenylenediisopropylidene)bisaniline (BisP), 4,4'-(1,3-phenylenediisopropylidene)bisaniline (BisM), and 9,9'-bis(4-aminophenyl)fluorene (BAPF). In one embodiment, the dianhydride is selected from the group consisting of benzophenone-3,3',4,4'-biphenyltetracarboxylic dianhydride (BTDA), 2,2'-bis(3,4'-dicarboxyphenyl)hexafluoropropane dianhydride (6FDA), 3,3,'4,4'-biphenyltetracarboxylic dianhydride (BPDA), pyromellitic dianhydride (PMDA), 4,4'-oxydiphthalic anhydride (ODPA), or a combination of two or more thereof.

A method for synthesizing a polyimide aerogel having reduced shrinkage is also described herein. According to an aspect of the innovation, the method of synthesizing comprises dissolving at least one diamine (a) in a first solvent to form a first solution; adding a dianhydride (b) to the first solution to form a second solution; adding a cardo-diamine (c) to the second solution; adding a non-nucleophilic base to the second solution to form an imidized oligomer; adding a cross-linking agent to the solution containing the imidized oligomer; allowing the solution to gel; and subjecting the gel to supercritical drying.

According to one embodiment, a diamine is dissolved in a first solvent to form a first solution. In one embodiment, the diamine is 4,4'-oxydianiline (ODA). In one embodiment, the first solvent is anhydrous N-methylpyrrolidone (NMP).

In one embodiment, after the diamine has been dissolved in the first solvent, a dianhydride is added to the first solution to form a second solution. In one embodiment, the dianhydride is 3,3',4,4'-biphenyltetracarboxylic dianhydride (BPDA). After the addition of the dianhydride (e.g., BPDA), the resulting solution should consist mostly of the n=1 oligomer, e.g., BPDA-ODA-BPDA, plus some excess BPDA.

According to one embodiment, after the addition of the dianhydride, a cardo-diamine is added. In one embodiment, the cardo-diamine includes a bulky fluorene moiety. In one embodiment, the cardo-diamine is 9,9'-bis(4-aminophenyl)fluorene (BAPF). Upon the addition of the cardo-diamine (e.g., BAPF), a polyamic acid oligomer with a largely alternating arrangement is produced. For example, BAPF-(BPDA-ODA-BPDA-BAPF).

In one embodiment, trimethylamine and acetic anhydride are then added to the polyamic acid solution, resulting in the imidization of the oligomer. Once the imidized oligomers form, a cross-linker is added. In one embodiment, the crosslinker is benzenetricarbonyl trichloride (BTC). In another embodiment, the BTC is dissolved in NMP prior to addition. The resulting solution is then allowed to gel.

In another aspect of the innovation, the resulting gel may be subject to supercritical drying. In one embodiment, prior to supercritical drying, the gel may be first placed in a first soaking solvent for a set amount of time. In one embodiment, the gel is soaked for about 4 hours, about 6 hours, about 12 hours, about 24, or about 48 hours. In one embodiment, the first soaking solvent may be replaced with a second soaking solvent and the gel allowed to soak in the second soaking solvent for about 4 hours, about 6 hours, about 12 hours, about 24, or about 48 hours. In one embodiment, the second soaking solvent may be replaced with a 100% acetone solution and the gel allowed to soak for about 4 hours, about 6 hours, about 12 hours, about 24, or about 48 hours. Up to four more solvent exchanges in 100% acetone may take place in time intervals of about 4 hours, about 6 hours, about 12 hours, about 24, or about 48 hours.

After soaking in the solvent(s) the gel may be supercritically dried. In one embodiment, the gel is supercritically dried using liquid $CO_2$ extraction, followed by drying under vacuum for about 4 hours, about 6 hours, about 12 hours, about 24, or about 48 hours.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIG. 9A shows the empirical model for the compressive modulus (MPa) of embodiments of aerogels as a function of polymer concentration (%) and content of BAPF (%) and FIG. 9B shows the log-log plot of modulus vs density as a function of polymer concentration and BAPF concentration.

(FIG. 13B), comparing previous results with those of embodiments of the ODA/BAPF compositions of the innovation.

DETAILED DESCRIPTION

Figure 1:
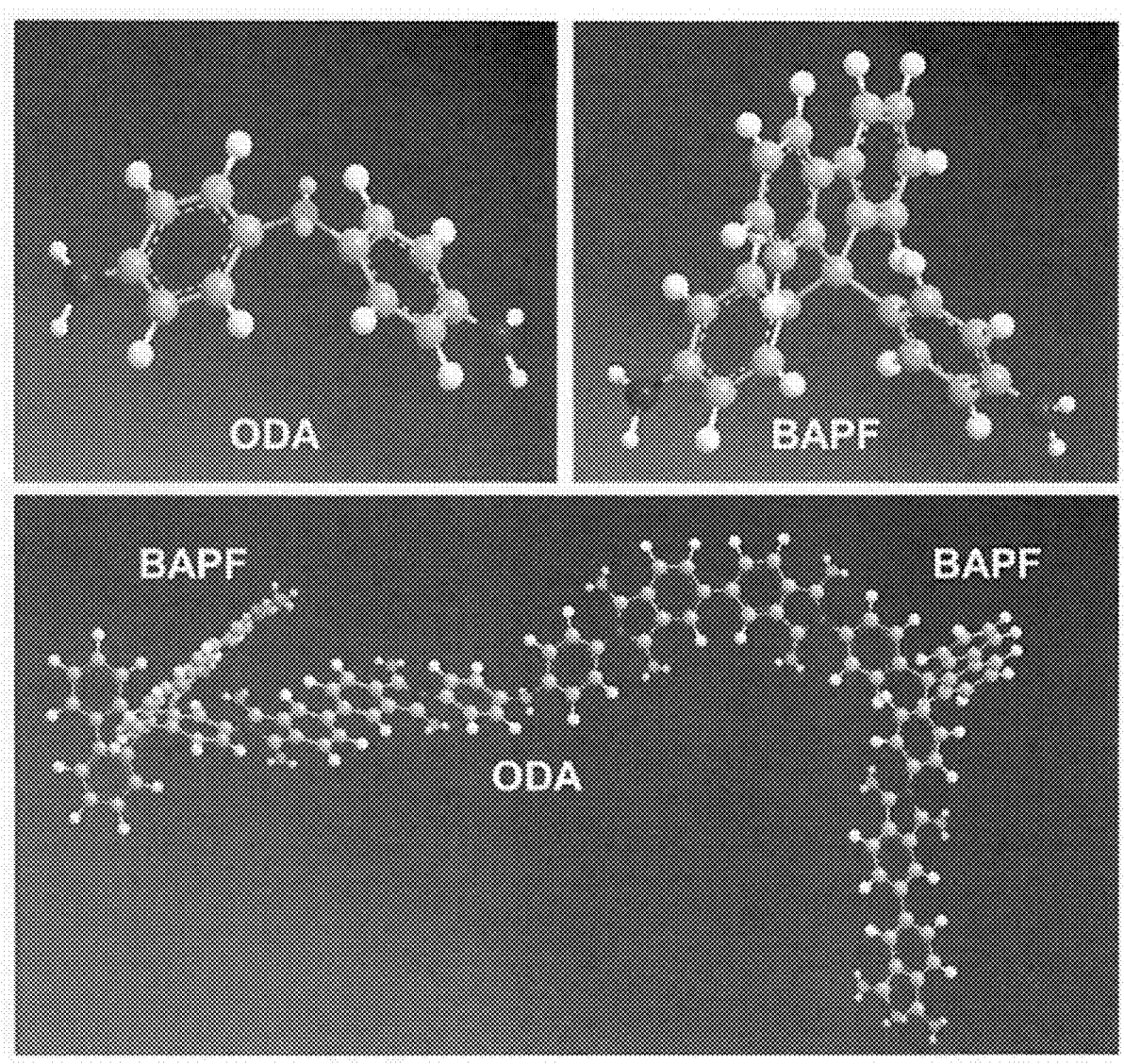
FIG. 1 depicts three-dimensional ball and stick models for the monomers 4,4'-oxydianiline (ODA) and 9,9'-bis(4-aminophenyl)fluorene (BAPF) and the conformation of the polyimide chain comprising both monomers.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

While specific characteristics are described herein (e.g., thickness, orientation, configuration, etc.), it is to be understood that the features, functions and benefits of the innovation can employ characteristics that vary from those described herein. These alternatives are to be included within the scope of the innovation and claims appended hereto. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

What follows is a more detailed discussion of certain compositions, articles, methods, materials, and apparatuses associated with aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the experiments and associated setups—such as choice of materials (e.g., selection of diamine(s) or diacid chloride(s), solvent(s), relative concentration of isomers, etc.), solid concentration, repeat units, etc.—the compositions, articles, and methods described herein can be employed in other contexts, as well. For example, various aspects of the subject innovation can be utilized to produce aerogels for a variety of uses terrestrial or otherwise (e.g., as insulators, as low dielectric substrates, etc.). In some embodiments, different selections of materials or formulation parameters can be selected than those used in the experiments discussed herein, and may have differing characteristics, as explained in greater detail below.

Polyimide aerogels are robust, low density materials with excellent insulation properties and low dielectric constants, making them useful as thermal or electrical insulation for any number or aerospace or terrestrial applications. In one embodiment, the polyimide aerogel can be used in aeronautics and for space exploration purposes. For example, the polyimide aerogel can be used in cryotank insulation, fan engine containment (ballistic protection), antenna substrate, building structures for habitats or vehicles (e.g., rovers), propellant tanks, heat shielding, inflatable aerodynamic decelerators, sandwich structures with two relatively thin, stiff and strong face sheets with the aerogel as a lightweight core material, and insulation for extravehicular activity (EVA) suits and habitats.

The innovation may be used to improve the thermal aging characteristics of polyimide aerogels which have been contemplated for use as insulation for inflatable aerodynamic decelerators, as tank insulation, as insulation for EVA suits, as onboard insulation for the warm electronic boxes of rovers, as well as for low dielectric substrates for aircraft antennas.

The innovation disclosed herein is an innovative polyimide aerogel and method of making same. The innovation also includes a method for reducing thermally induced shrinkage of polyimide aerogels using rigid cardo-diamine moieties in the polymer chain. These rigidified polymer chains are cross-linked to create a network structure that gels in solution. This gel can be dried into a polyimide aerogel that is less susceptible to thermally induced shrinkage.

This innovation describes a method for improving the dimensional stability of polyimide aerogels at elevated temperatures for extended periods of time utilizing a space-filling, rigid cardo-diamine in the polymer backbone to stiffen the polymer chain. The rigidified polymer chain is less susceptible to thermally induced motion that ultimately results in shrinkage and densification of the aerogel. In one embodiment, the cardo-diamine reacts with the dianhydride in the same fashion as a linear diamine to produce a poly(amic acid) intermediate which then undergoes imidization chemically through the addition of acetic anhydride and triethylamine.

In one embodiment, the addition of cardo-diamine replaces a certain fraction of less sterically hindered diamine in the typical polyimide synthesis and does not change any of the developed and documented chemistries or processes. For this reason, fabrication of the gel can be scaled up and translated into a continuous process for making roll to roll films or molded products as demonstrated by other polyimide formulations.

In one aspect, up to 75% of a diamine used in prior polyimide aerogel synthesis can be substituted with a cardo-diamine as described herein. The resulting polyimide aerogel exhibits dramatically reduced thermally induced shrinkage compared to previously available polyimide aerogels.

In another aspect of the innovation, the polyimide aerogel can be preconditioned at the use temperature (i.e., the anticipated temperature as which the aerogel will be primarily used) to stabilize shrinkage. Preconditioning can take place at about 150° C. or about 200° C. over a period of 24 to 48 hours.

In one aspect of the innovation, the incorporation of a bulky, space-filling moiety into the polymer backbone reduces thermal shrinkage in a polyimide aerogel. Bulky groups are considered to be sterically hindering which can disrupt certain chemical reactions as well as rotation about chemical bonds. Bulky moieties include: adamantyl, triptycene, phenolphthalein (PPH), anthrone, fluorene, and norbornane groups. In one embodiment, the bulky, space-filling molecule 9,9'-bis(4-aminophenyl)fluorene (BAPF) which contains the fluorene moiety. BAPF may be particularly suitable as a bulky cardo-diamine because it contains the rigid polycyclic fluorene moiety having limited bond rotation.

The innovative polyimide aerogels showed a reduction in thermally induced shrinkage by as much as 50% compared to polyimide aerogels that do not contain BAPF. FIG. 1 depicts three-dimensional ball and stick models for the monomers 4,4'-oxydianiline (ODA) and BAPF and the conformation of the polyimide chain comprising both monomers according to an embodiment of the innovation.

In one aspect of the innovation, the polyimide aerogel has reduced temperature induced shrinkage. The polyimide aerogel comprises an oligomer backbone with n repeating units. In one embodiment, n is at least 10. In another embodiment, n is in the range of about 20 to about 40 repeating units. In yet another embodiment, n is at least 30.

In an aspect of the innovation, the oligomer backbone includes a cardo-diamine. In one embodiment, the cardo-diamine includes a bulky fluorene moiety. Other bulky moieties include: anthrone, phenolphthalein (PPH), imide version of phenolphthalein (PPH), norbornane, cyclohexane, or a combination of two or more thereof. Suitable cardo-diamines include 9,9'-bis(4-aminophenyl)fluorene, 9,9'-bis(4-amino-3-methylphenyl)fluorene, 9,9'-bis(3-ethyl-4-aminophenyl)fluorene, 9,9'-bis(4-amino-3-fluorophenyl)fluorene, 9,9'-bis(4-amino-3-chlorophenyl)fluorene, 9,9'-bis(3-amino-4-hydroxyphenyl)fluorene, 3,3'-bis(4-aminophenyl)phthalide, and 1,1'-bis(4-aminophenyl)cyclohexane. In one embodiment, the cardo-diamine is 9,9'-bis(4-aminophenyl)fluorene (BAPF).

In one embodiment, the cardo-diamine comprises at least about 10 mol %; at least about 20 mol %; at least about 30 mol %; at least about 40 mol %; at least about 50 mol %; at least about 60 mol %; or even at least about 70 mol % of the backbone In another embodiment, the polymer concentration is at least about 5 wt %, at least 6 wt %, at least about 7 wt %, at least about 8 wt %, at least about 9 wt %, at least about 10 wt %, at least about 11 wt %, at least about 12 wt %, at least about 13 wt %, at least about 14 wt %, or at least 15 wt %. In another embodiment, the polymer concentration is in the range of about 5 wt % to about 20 wt %; about 5 wt % to about 15 wt %, or about 5 wt % to about 10 wt %. In one embodiment, the polymer concentration is in the range of about 7 wt % to about 15 wt % or from about 7 wt % to about 10 wt %.

The repeating unit may comprise at least one diamine and one dianhydride. In one embodiment, the diamine is selected from the group consisting of 2,2'-bis[4-(4-aminophenoxy)phenyl]propane (BAPP), 3,4'-oxydianiline (3,4'-ODA), 4,4'-oxydianiline (4,4'-ODA), p-phenylene diamine (PPDA), 2,2'-dimethylbenzidine (DMBZ), bisaniline-p-xylidene (BAX), 4,4'-bis(4-aminophenoxy)biphenyl (4,4'-BAPB), 3,3'-bis(4-aminophenoxy)biphenyl (3,3'-BAPB), 4,4'-(1,4-phenylenediisopropylidene)bisaniline (BisP), 4,4'-(1,3-phenylenediisopropylidene)bisaniline (BisM), and 9,9'-bis(4-aminophenyl)fluorene (BAPF). In one embodiment, the dianhydride is selected from the group consisting of benzophenone-3,3',4,4'-tetracarboxylic dianhydride (BTDA), 2,2'-bis(3,4'-dicarboxyphenyl)hexafluoropropane dianhydride (6FDA), 3,3',4,4'-biphenyltetracarboxylic dianhydride (BPDA), and pyromellitic dianhydride (PMDA), pyromellitic dianhydride (PMDA), 4,4'-oxydiphthalic anhydride (ODPA), or a combination of two or more thereof.

A method for synthesizing a polyimide aerogel having reduced shrinkage is also described herein. According to an aspect of the innovation, the method of synthesizing comprises dissolving at least one diamine (a) in a first solvent to form a first solution; adding a dianhydride (b) to the first solution to form a second solution; adding a cardo-diamine (c) to the second solution; adding a non-nucleophilic base to the second solution to form an imidized oligomer; adding a cross-linking agent to the solution containing the imidized oligomer; allowing the solution to gel; and subjecting the gel to supercritical drying.

Figure 2:
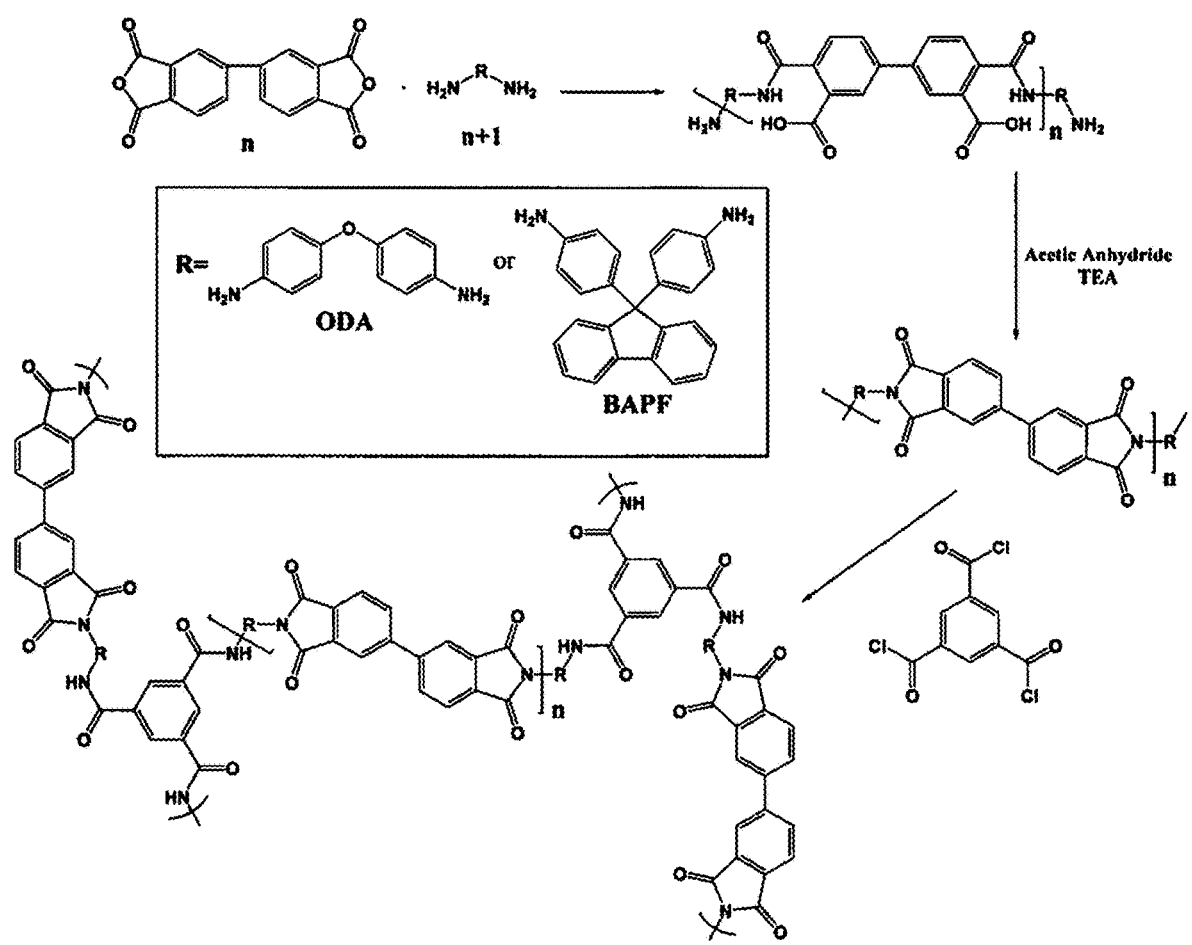
FIG. 2 is a schematic drawing representing an embodiment of the method of synthesis of cardo-diamine-containing polyimide aerogels.

FIG. 2 depicts a schematic showing the synthesis of a polyimide aerogel according to an embodiment of the innovation. According to one embodiment, a diamine is dissolved in a first solvent to form a first solution.

Suitable diamines include 2,2'-bis[4-(4-aminophenoxy)phenyl]propane (BAPP), 3,4'-oxydianiline (3,4'-ODA), 4,4'-oxydianiline (4,4'-ODA), p-phenylene diamine (PPDA), 2,2'-dimethylbenzidine (DMBZ), bisaniline-p-xylidene (BAX), 4,4'-bis(4-aminophenoxy)biphenyl (4,4'-BAPB), 3,3'-bis(4-aminophenoxy)biphenyl (3,3'-BAPB), 4,4'-(1,4-phenylenediisopropylidene)bisaniline (BisP), 4,4'-(1,3-phenylenediisopropylidene)bisaniline (BisM), and 99'-bis(4-aminophenyl)fluorene (BAPF). In one embodiment, the diamine is 4,4'-oxydianiline (ODA). The solvent may be a polar aprotic solvent chosen from: nitrobenzene, benzonitrile, sulfolane, α-chloronapthalene, tricresol, and n-methyl-2-pyrrolidone. In one embodiment, the first solvent is anhydrous N-methylpyrrolidone (NMP).

In one embodiment, after the diamine has been dissolved in the first solvent, a dianhydride is added to the first solution to form a second solution. A suitable dianhydride may be selected from the group consisting of benzophenone-3,3',4,4'-tetracarboxylic dianhydride (BTDA), 2,2'-bis(3,4'-dicarboxyphenyl)hexafluoropropane dianhydride (6FDA), 3,3',4,4'-biphenyltetracarboxylic dianhydride (BPDA), pyromellitic dianhydride (PMDA), or a combination of two or more thereof. In one embodiment, the dianhydride is 3,3',4,4'-biphenyltetracarboxylic dianhydride (BPDA). After the addition of the dianhydride (e.g., BPDA), the resulting solution should consist mostly of the n=1 oligomer, e.g., BPDA-ODA-BPDA, plus some excess BPDA.

According to one embodiment, after the addition of the dianhydride, a cardo-diamine is added. In one embodiment, the cardo-diamine includes a bulky fluorene moiety. Suitable cardo-diamines include: cardo-anthrone, cardo-phenolphthalein (PPH), cardo-norbornane, cardo-cyclohexane, and cardo-fluorene groups. In one embodiment, the cardo-diamine is 9,9'-bis(4-aminophenyl)fluorene (BAPF). Upon the addition of the cardo-diamine (e.g., BAPF), a polyamic acid oligomer with a largely alternating arrangement is produced. For example, BAPF-(BPDA-ODA-BPDA-BAPF).

In one embodiment, an alternating co-polymer may be formulated by adding stoichiometric amounts of ODA followed by BAPF.

In one embodiment, trimethylamine and acetic anhydride are then added to the polyamic acid solution, resulting in the imidization of the oligomer. Once the imidized oligomers form, a cross-linker is added. Suitable cross-linkers include, but are not limited to: 1,3,5-triaminophenoxybenzene (TAB), 2,4,6-tris(4-aminophenyl)pyridine (TAPP), octa-(aminophenoxy)silsesquioxane (OAPS), or 1,3,5-tris-(aminophenyl)benzene (TAPB). Polyfunctional aliphatic isocyanates, as well as triacid chlorides such as 1,3,5-benzenetricarbonyl trichloride (BTC) have been used for amine end-capped polyimide oligomers. In one embodiment, the crosslinker is benzenetricarbonyl trichloride (BTC). In another embodiment, the BTC is dissolved in NMP prior to addition. The solution is then allowed to gel.

Table 1 provides additional examples of polyimide aerogels according to the innovation. It will be appreciated that other variations, including to the concentration of components and the timing of their addition, that are encompassed by the innovation.

In another aspect of the innovation, the resulting gel may be subject to supercritical drying. In one embodiment, prior to supercritical drying, the gel may be first placed in a first soaking solvent for a set amount of time. In one embodiment, the gel is soaked for about 4 hours, about 6 hours, about 12 hours, about 24, or about 48 hours. In one embodiment, the first soaking solvent may be replaced with a second soaking solvent and the gel allowed to soak in the second soaking solvent for about 4 hours, about 6 hours, about 12 hours, about 24, or about 48 hours. In one embodiment, the second soaking solvent may be replaced with a 100% acetone solution and the gel allowed to soak for about 4 hours, about 6 hours, about 12 hours, about 24, or about 48 hours. Up to four more solvent exchanges in 100% acetone may take place in time intervals of about 4 hours, about 6 hours, about 12 hours, about 24, or about 48 hours.

After soaking in the solvent(s) the gel may be supercritically dried. In one embodiment, the gel is supercritically dried using liquid $CO_2$ extraction, followed by drying under vacuum at a temperature of about 70° C. to about 95° C. for about 4 hours, about 6 hours, about 12 hours, about 24, or about 48 hours. It may also be possible to extract the solvent from the gels using freeze drying or ambient drying in some cases.

Figure 3:
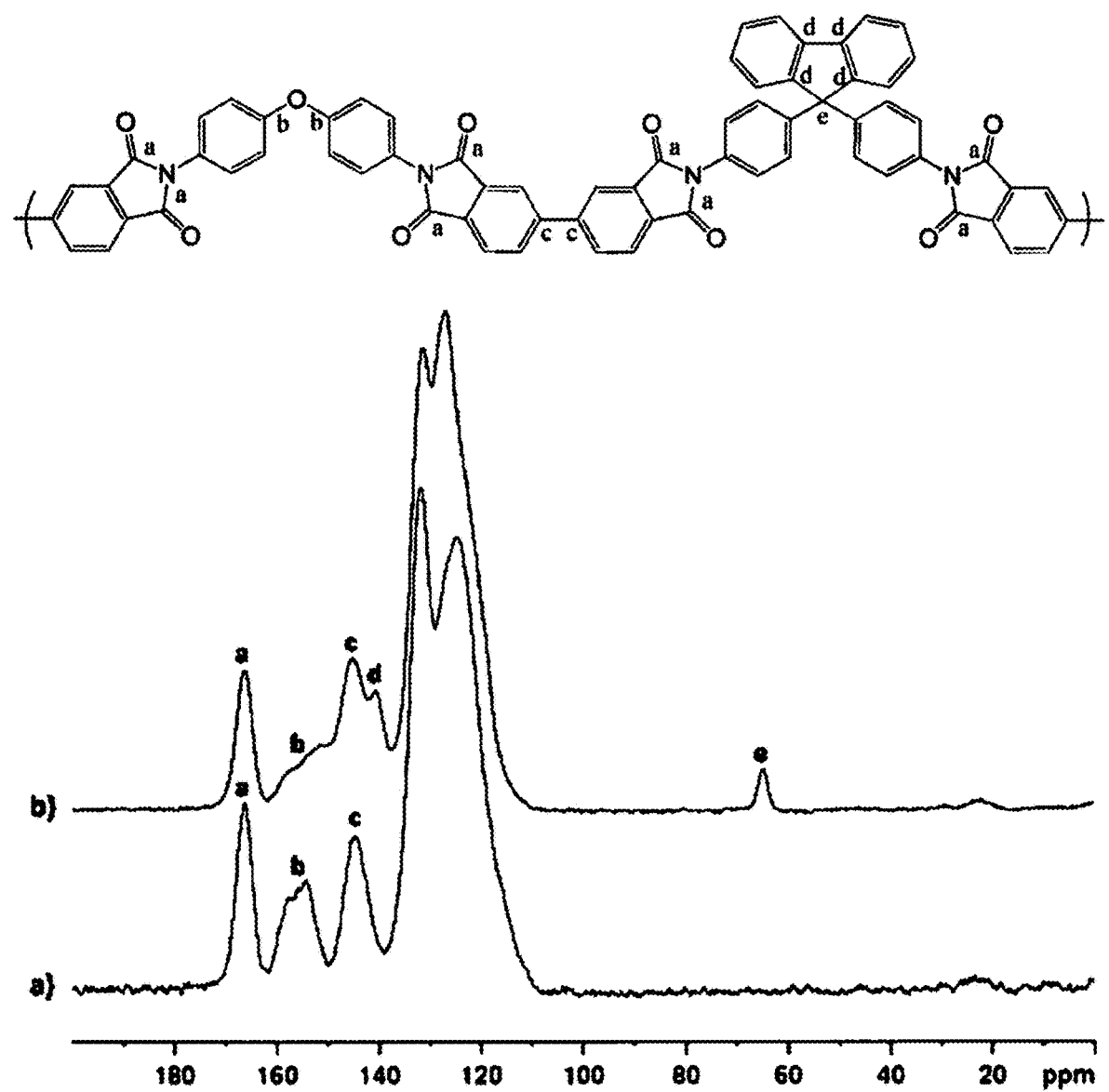
FIG. 3. Depicts $^{13}C$ solid-state NMR spectra of embodiments of aerogels according to the innovation as provided in Table 1: (a) sample 8 (0 mol % BAPF, 10 wt %, n=40); (b) sample 18 (50 mol % BAPF, 10 wt %, n=40).

FIG. 3 shows the $^{13}C$ solid state NMR spectra of two representative samples formulated with n of 40 and 10 wt % polymer concentration, made with no BAPF (sample 8, spectrum a) and 50 mol % BAPF (sample 18, spectrum b). The sharp peaks at 1653 ppm (imide carbonyl, peak a) and 143 ppm (quaternary aromatic, peak c) and the broad peaks from 115 to 138 (nonquaternary aromatics) are present in both spectra, as expected. The peak at 153 ppm (quaternary aromatic attached to oxygen, peak b) also appears in both spectra but is larger in spectrum a) because this sample contains twice the amount of ODA. There are two peaks present exclusively in spectrum b that are assigned to carbons in BAPF, at 141 ppm (quaternary aromatics in fluorene unit, d) and 65 ppm (aliphatic carbon in fluorene unit, e).

Scanning electron micrographs of representative aerogels made with 7 wt % polymer concentration are shown in FIG. 4. As with other polyimide aerogels, the architecture is composed of an open porous network with a homogeneous fibrillar appearance. Formulations containing higher polymer concentrations have an appearance similar to that of the 7 wt % samples shown here, but they appear slightly less porous. In general, samples containing no BAPF are similar in morphology to those containing 50 mol % BAPF.

Figure 5A:
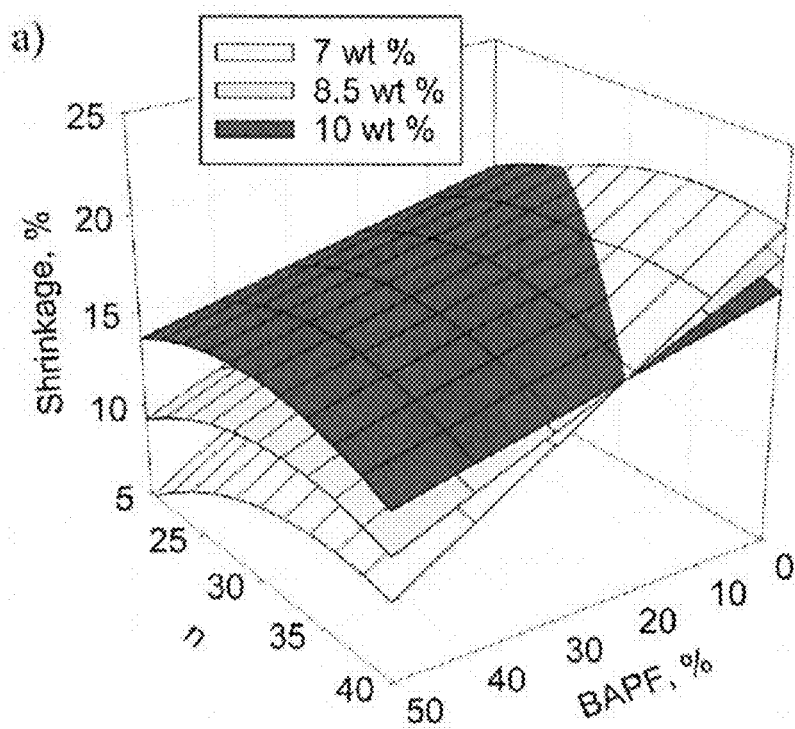
FIGS. 5A and 5B are graphs showing shrinkage (FIG. 5A) and (FIG. 5B) density as a function of n-value and BAPF content for three levels of polymer concentration.

FIG. 5 shows the empirical models for shrinkage occurring during fabrication (standard deviation=1.46%, R2=0.91) and density (standard deviation=0.01 g/cm³, R2=0.89) of all of the samples as set forth in Table 1. The plot of the shrinkage as a function of the n-value and BAPF concentration (cardo-diamine) for each of the three polymer concentrations (FIG. 5A) shows that increasing the concentration of BAPF significantly reduces shrinkage but more so at lower polymer concentrations. Samples containing 0 mol % BAPF shrank approximately 20%, whereas samples containing 50 mol % BAPF shrank as little as 5%. Without being bound to any particular theory, it is possible that the reduction in shrinkage may be due to the effect of BAPF on the chain packing. The polymer chains may adopt a kinked conformation with less tightly packed networks that keep the aerogel from shrinking during processing. The n-value has a small, though significant, effect on the observed shrinkage.

Figure 5B:
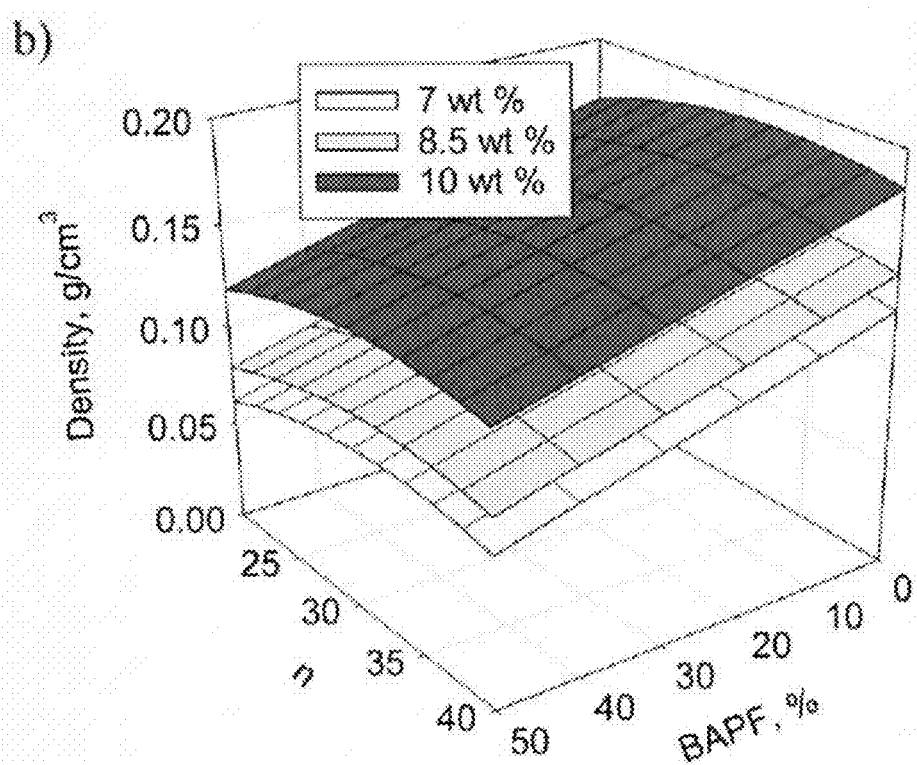

Because the degree of shrinkage affects the density of each sample, it is expected that the density model shown in FIG. 5B would be very similar to FIG. 5A. Increasing the fraction of BAPF does cause a significant decrease in density as expected. However, there is no significant synergistic effect between polymer concentration and BAPF concentration as was seen with shrinkage. In other words, density increases with increasing BAPF concentration to the same extent for all polymer concentrations. This may indicate that lower concentrations lead to a loss of some low molecular weight material during washing and supercritical drying, especially at higher BAPF concentrations.

Figure 6:
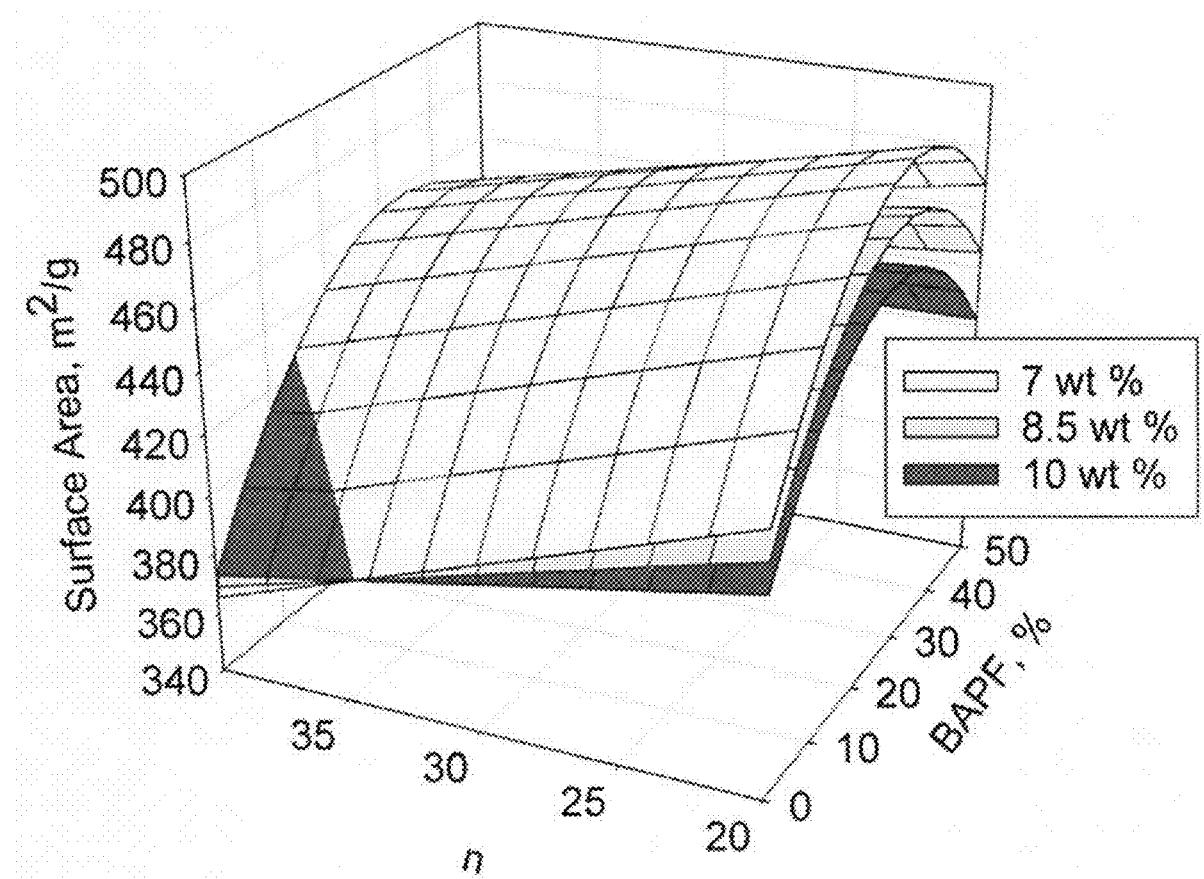
FIG. 6 is a graph of the empirical model of surface area ($m^2$/g) as a function of n-value and BAPF content (%) for the three levels of polymer concentration.

BET surface areas were obtained for all of the samples using nitrogen sorption. The empirical model for surface area, FIG. 6 with increasing polymer concentration and increasing n. In addition, surface area increases with BAPF concentration but reaches a predicted maximum at 30 mol %. It is expected that BAPF would increase the microporosity and therefore the surface area of the polymer strands by disrupting chain packing, but it may be that increasing BAPF beyond 35% causes an increase in larger pore sizes.

Figure 7:
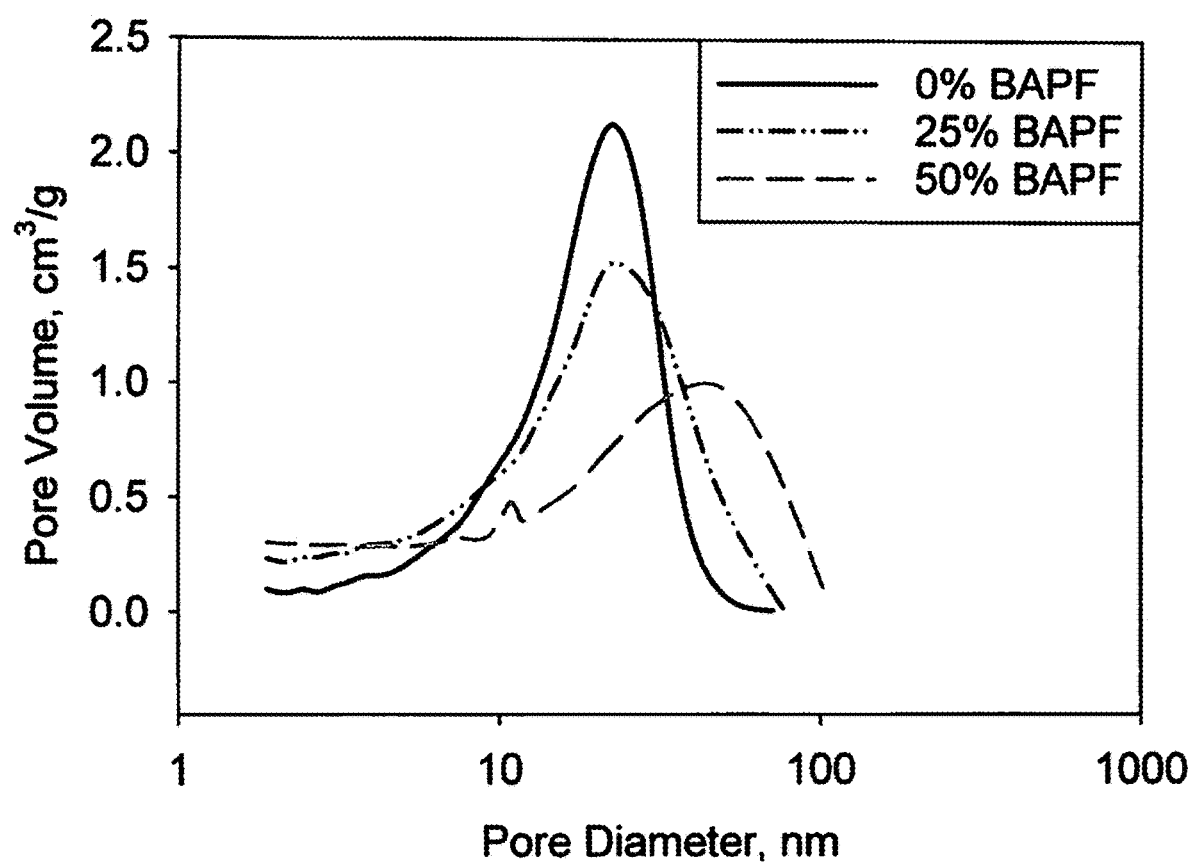
FIG. 7 is a plot of the pore volume ($cm^3$/g) as a function of pore diameter (nm) for sample 14 according to Table 1 containing 7 wt % polymer concentration, 100% ODA, and an n-value of 40 and sample 15 according to Table 1 containing 7 wt % polymer concentration, 50% ODA/50% BAPF, and an n-value of 40.

FIG. 7 shows the pore size distributions for representative samples, whose SEM images are shown in FIG. 4. The sample made with 50 mol % BAPF possesses a wider pore size and more pores below 8 nm in size than the aerogels made using no BAPF. The sample made with 100% ODA has a narrower pore size distribution centered at 20-25 nm. The increase in small-scale porosity indicates that the addition of BAPF produces a significant number of small pores compared with samples containing 0% BAPF, but at the same time, the reduced shrinkage observed during processing also introduces an increase in the number of larger pores, accounting for the wider pore distribution in the BAPF-containing samples.

Figure 8:
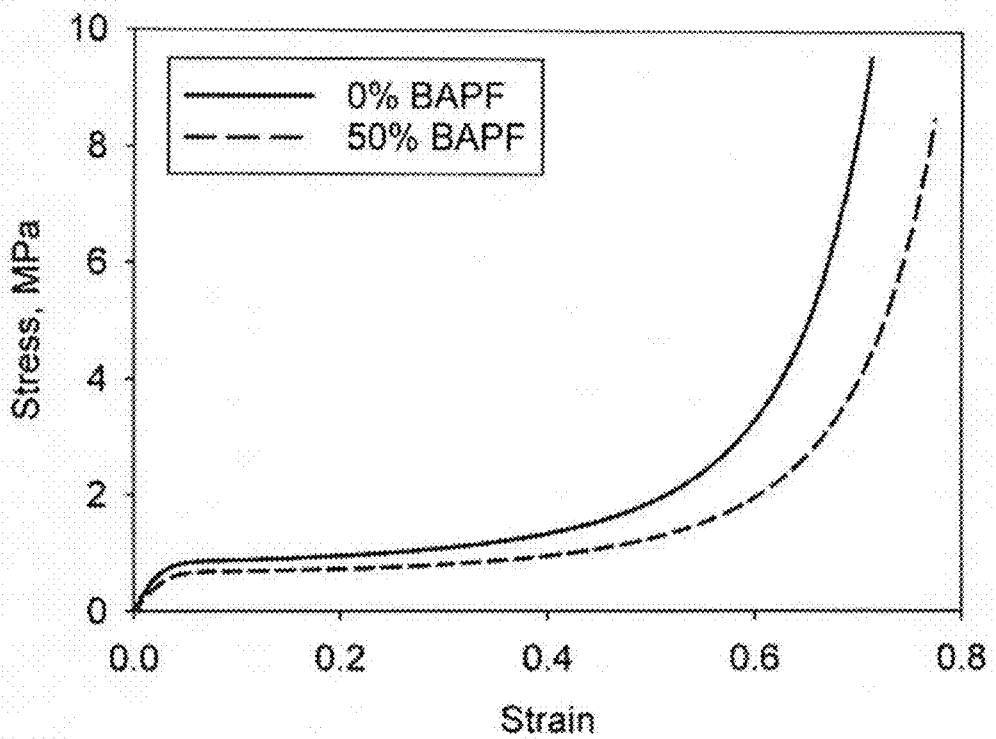
FIG. 8 is a graph depicting typical stress-strain curves for the compression of polyimide aerogel sample 8 (Table 1) ($\varrho$ =0.163 g/$cm^3$) and sample 18 (Table 1) ($\varrho$ =0.134 g/$cm^3$) (both formulations are made with n=40 and 10 wt % polymer concentration).

Compression testing was performed on all of the aerogels. Typical stress-strain curves are shown in FIG. 8, from representative samples made using 10 wt % polymer concentration, formulated n=40, and no BAPF (Table 1, sample 8) and 50 mol % BAPF (Table 1, sample 18). The Young's modulus is defined as the initial linear region of the stress-strain curve.

Figure 9A:
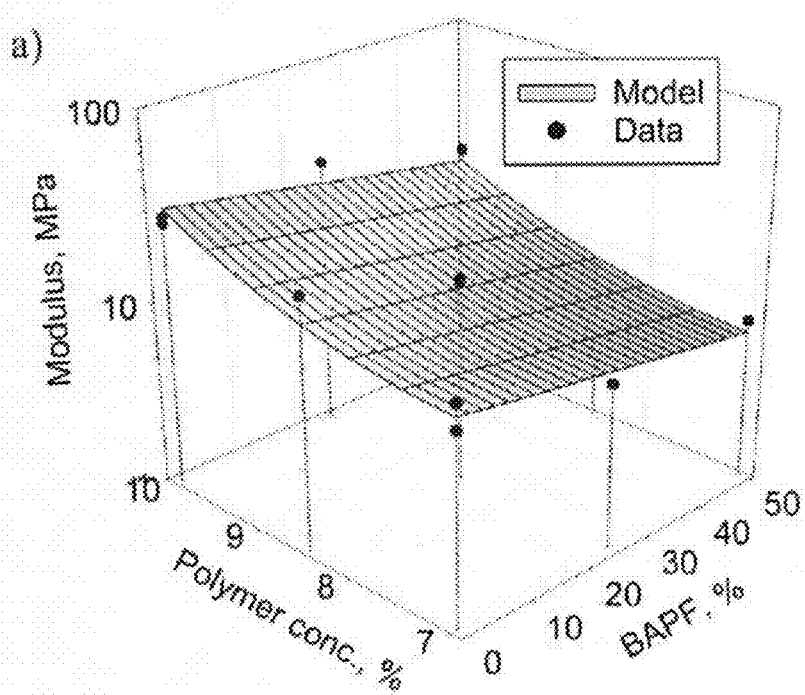
FIGS. 9A and 9B are graphs.
Figure 9B:
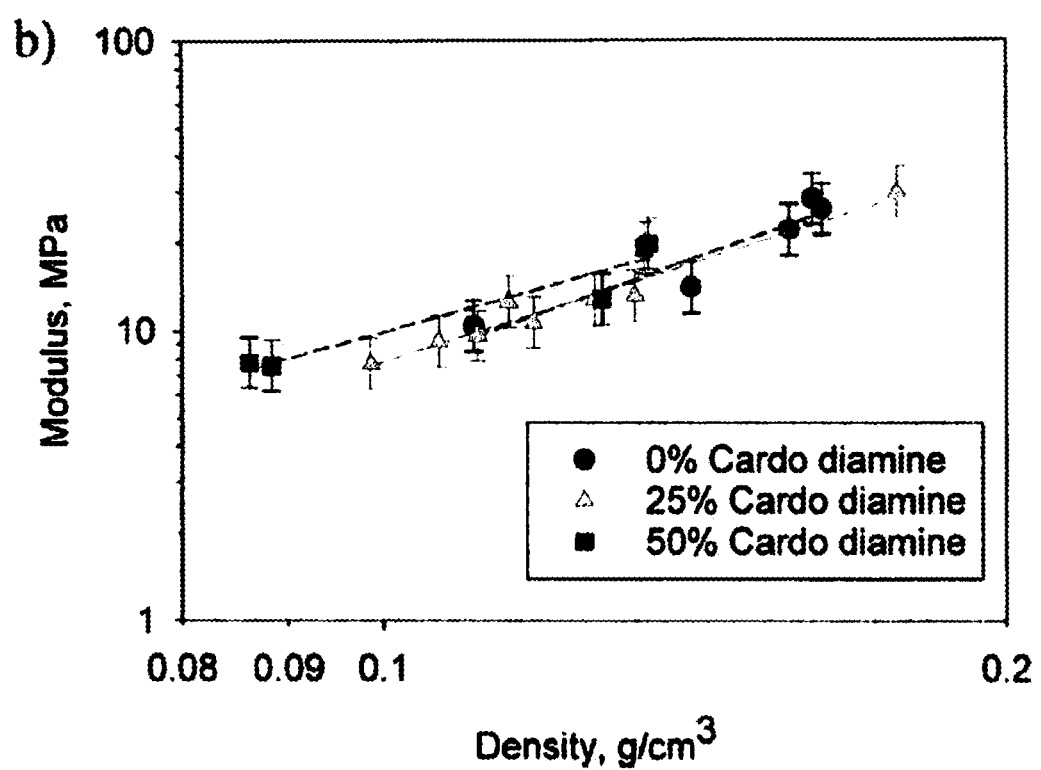
Figure 10A:
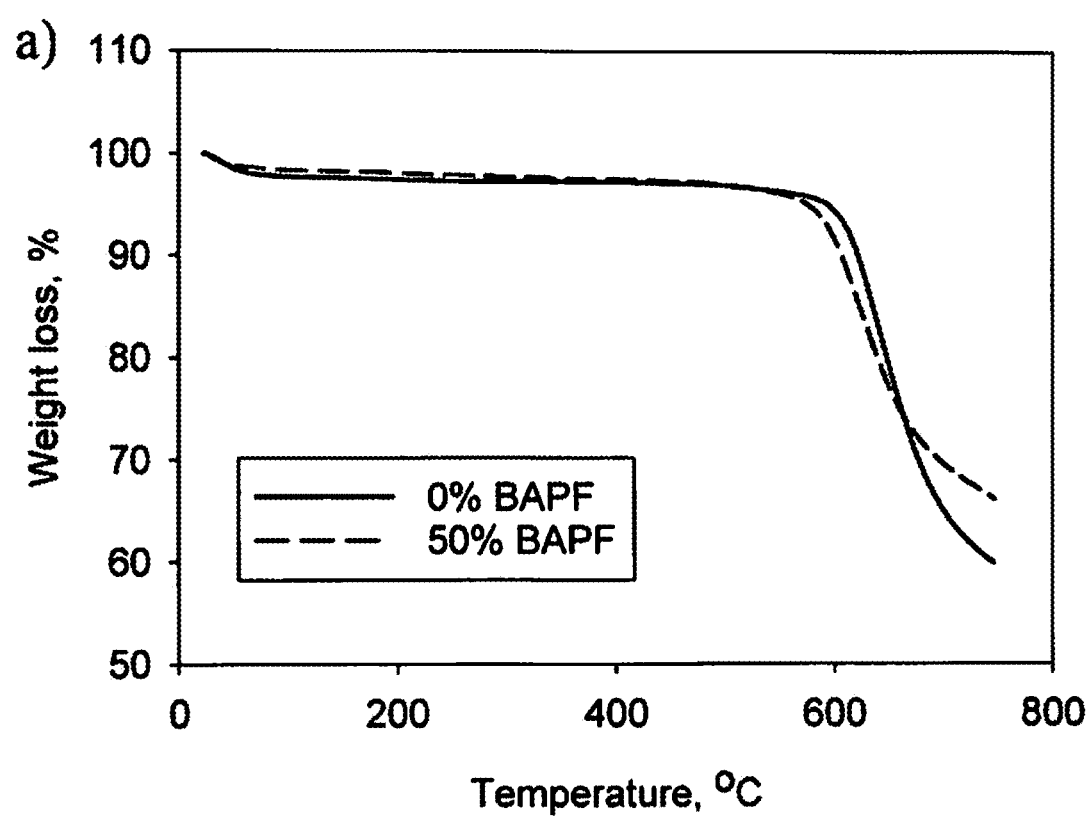
FIGS. 10A and 10B are graphs of representative TGA curves (FIG. 10A) and a plot of density (g/$cm^3$) as a function of time (hours) for isothermally aged samples at 200° C. containing 0% BAPF and 50% BAPF (FIG. 10B).

The empirical model for modulus (standard deviation=0.1 MPa, R2=0.84), shown in FIG. 9A, indicates a strong dependence on polymer concentration and concentration of BAPF but no significant effect of n over and above random error. The model shows that increasing the polymer concentration increases the modulus, while increasing the fraction of BAPF decreases the modulus. However, as seen in FIG. 9B, when density effects are accounted for in the plot of modulus as a function of density, increasing the content of BAPF actually slightly increases the modulus. Thus, the decrease in modulus with increasing BAPF seen may be due to the decrease in the density of the aerogels. FIG. 10A shows TGA plots of representative aerogel samples made using no BAPF (Table 1, sample 8) and 50 mol % BAPF (Table 1, sample 18). Incorporating BAPF into the polymer backbone slightly reduces the onset of decomposition temperatures from 598 to 585° C.

Figure 10B:
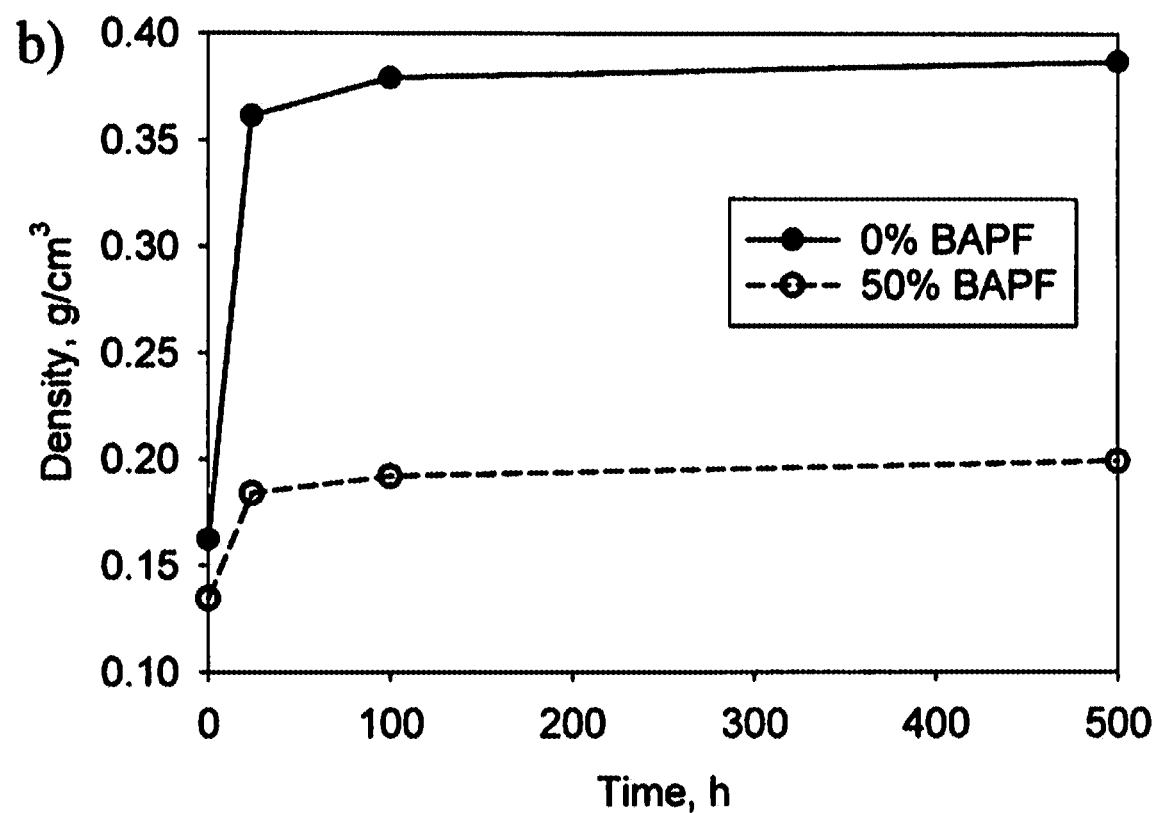

Use temperature is not limited, however, by the decomposition of the polymer backbones. Rather, it was found that during aging at temperatures as low as 150° C., the polyimide aerogels made with ODA or DMBZ in the backbone shrink. To assess the effect of aging on aerogels made with varying amounts of BAPF, isothermal aging was carried out for 500 h on all compositions at temperatures of 150 and 200° C. The samples were removed from the oven at 24 h, 100 h, and 500 h to measure changes in weight, density, and diameter shrinkage. The most significant changes in shrinkage and density occur within the first 24 h and then plateaued throughout the remainder of the study. FIG. 10B shows the same two representative samples of aerogel as shown in FIG. 10A made with no BAPF and 50 mol % BAPF. Because of shrinkage, the density of the aerogel made with no BAPF increases from 0.16 to 0.36 g/cm$^3$ in the first 24 h and remains fairly constant after that. In contrast, the density of the aerogel made using 50 mol % BAPF increased from 0.14 to 0.19 g/cm$^3$ over the 500 h. Very little weight loss (<1%) occurs over the same period for any of the aerogels; therefore, all of the density change is likely due to shrinkage.

Figure 11:
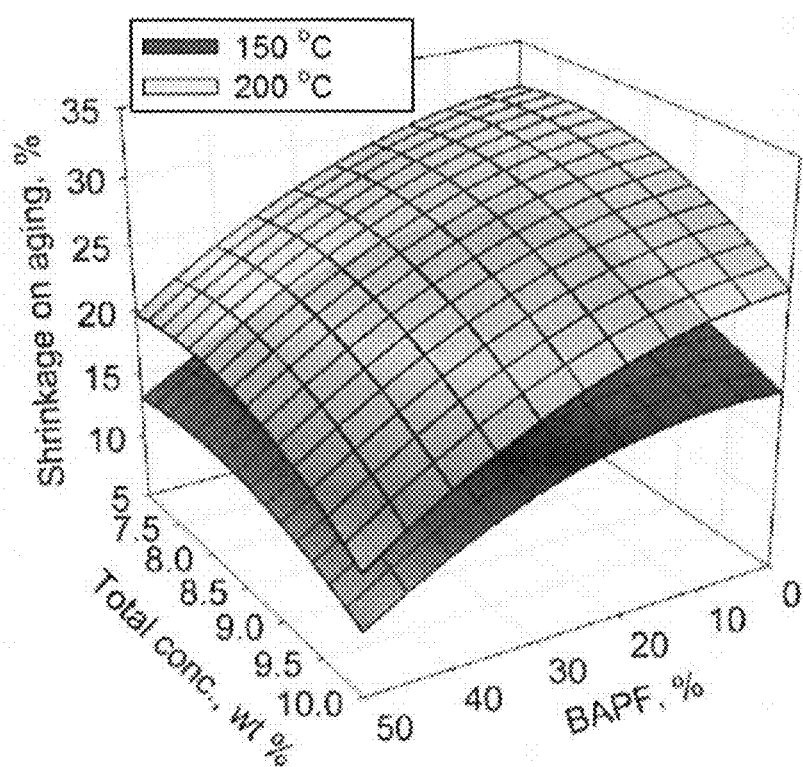
FIG. 11 is a graph showing the empirical model for shrinkage due to isothermal aging as a function of polymer concentration and BAPF concentration at 150 and 200° C.

As observed in the empirical model for shrinkage due to aging (standard deviation=2.72%, R$^2$=0.84) shown in FIG. 11, both polymer concentration and BAPF concentration have a significant effect. Shrinkage decreased with increasing polymer concentration and increasing BAPF concentration, with the lowest shrinkage (about 8%) occurring for samples made with 50 mol % BAPF and 10 wt % polymer. The n-value did not have a significant effect on shrinkage due to aging, over and above random error.

Figure 12A:
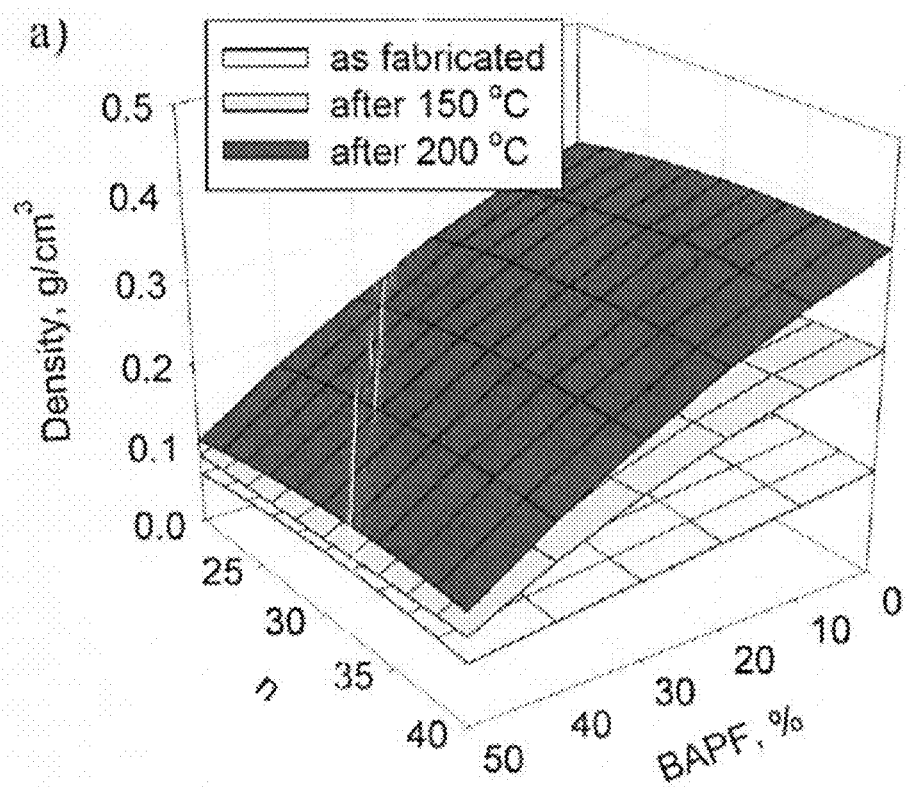
FIGS. 12A and 12B are graphs displaying the empirical models developed for density changes as fabricated, after 150° C., and after 200° C. as a function of n-value and mol % BAPF concentration at 7 wt % (FIG. 12A) and 10 wt % (FIG. 12B).
Figure 12B:
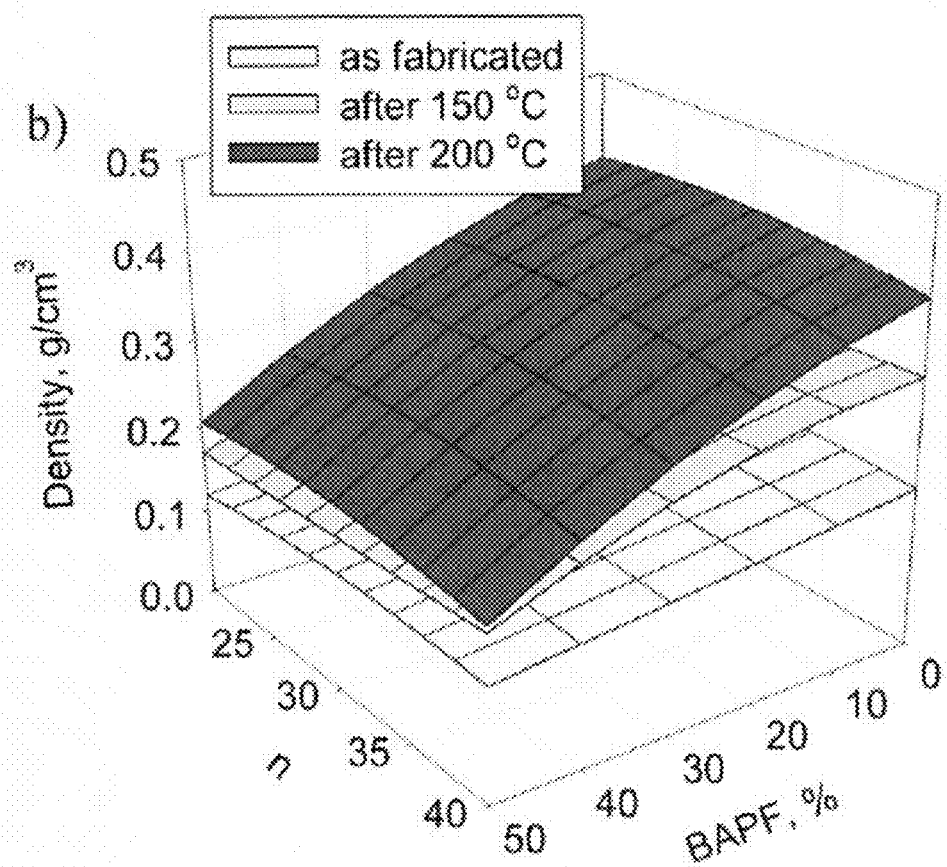

FIG. 12 shows the empirical models for density of the aerogels comparing as-fabricated densities to that observed after 500 h at 150 and 200° C. when polymer concentration is (a) 7 wt % and (b) 10 wt %. Both plots display density (g/cm$^3$) as a function of n-value and BAPF content (%) using the same density scale. It is clear that an increase in the content of BAPF results in a dramatic reduction in densification of the samples at elevated temperatures, which results from less shrinkage.

Figure 13A:
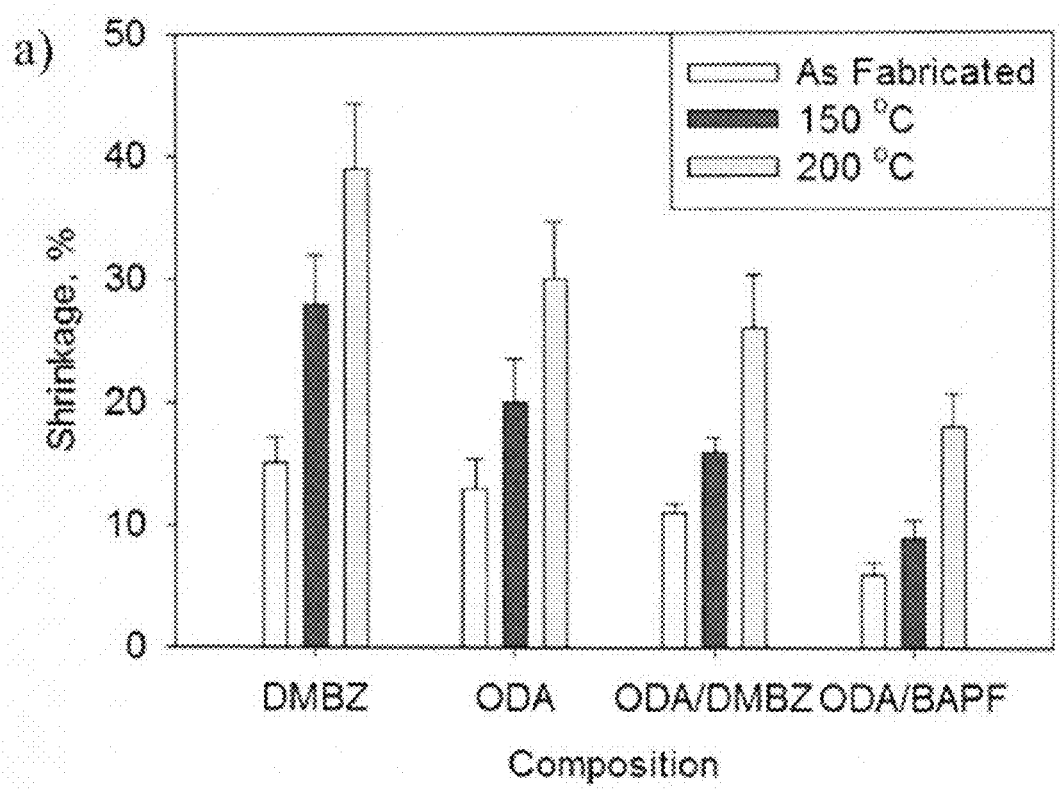
FIGS. 13A and 13B are bar graphs comparing the effect of diamine on isothermal shrinkage (%) (FIG. 13A) and the density after aging at 150 and 200° C.
Figure 13B:
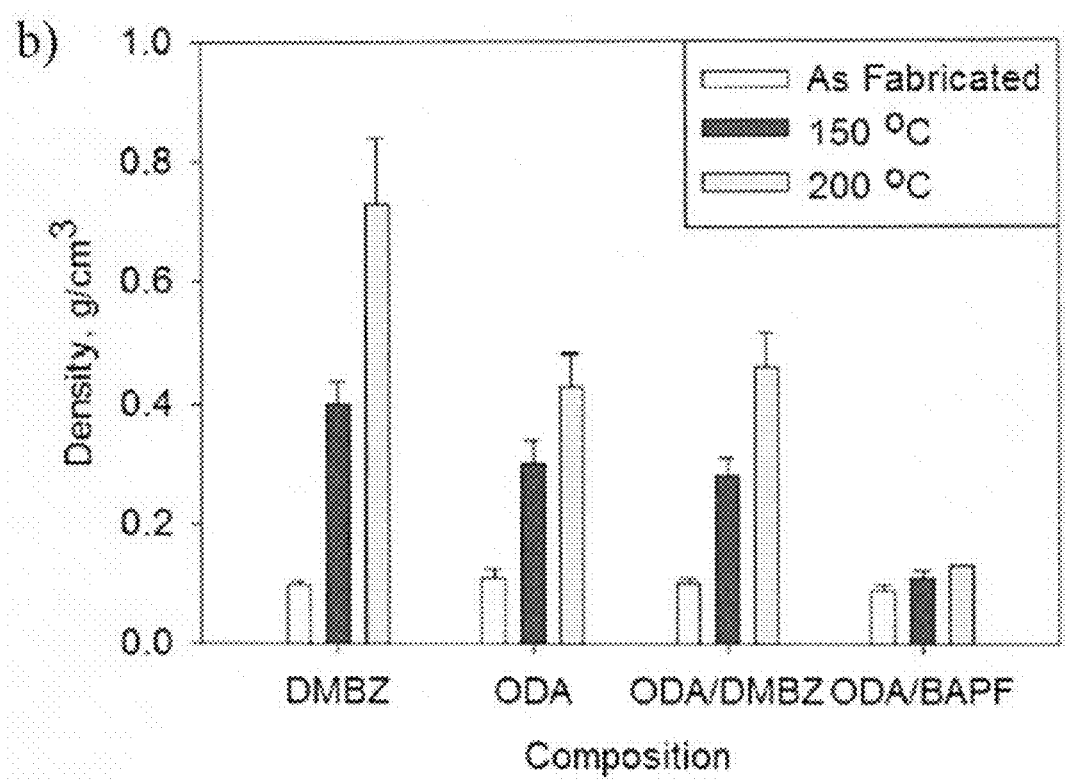

FIG. 13 presents the data from previous work comparing the shrinkage (a) and density (b) after aging for 500 h at 150 and 200° C. for samples made using DMBZ, ODA, or a combination of 50 mol % ODA/50 mol % DMBZ with the samples made using 50 mol % ODA/50 mol % BAPF according to the innovation. The samples made previously using ODA/DMBZ resulted in the lowest shrinkage and smallest density change after aging. This was attributed to disruption of polymer chain packing from the combination of flexible and rigid diamine segments. The combination of ODA/BAPF shrinks even less; thus, the density increase is much less compared to that previous aerogels.

Figure 14:
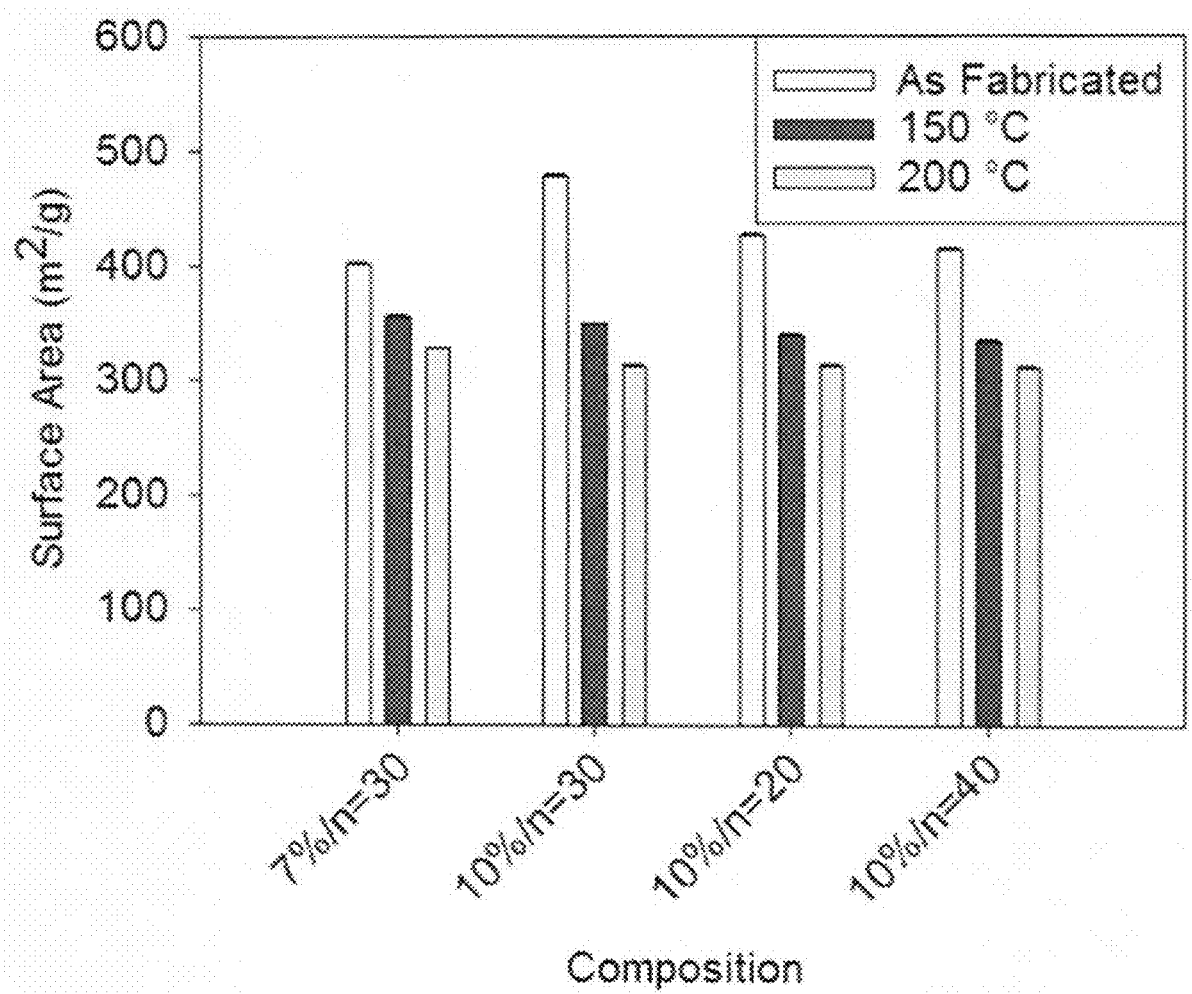
FIG. 14 is a bar graph comparing the surfaces areas as fabricated aerogels with the same aerogels after 500 h of isothermal aging at either 150° C. or 200° C. for selected samples made using 50 mol % BAPF.

As samples shrink, compaction of the pore structure will occur, which may result in decreased surface area. FIG. 14 compares the initial surface areas of representative samples made using 50 mol % BAPF to the surface areas after 500 h of aging. This selection of samples possesses a combination of good mechanical properties and the lowest values of shrinkage. As shown, the surface areas decrease during aging and with increasing aging temperature. However, even after 200° C. aging, the surface areas remain above 300 m$^2$/g, suggesting that the pore structure remains largely intact.

Figure 15:
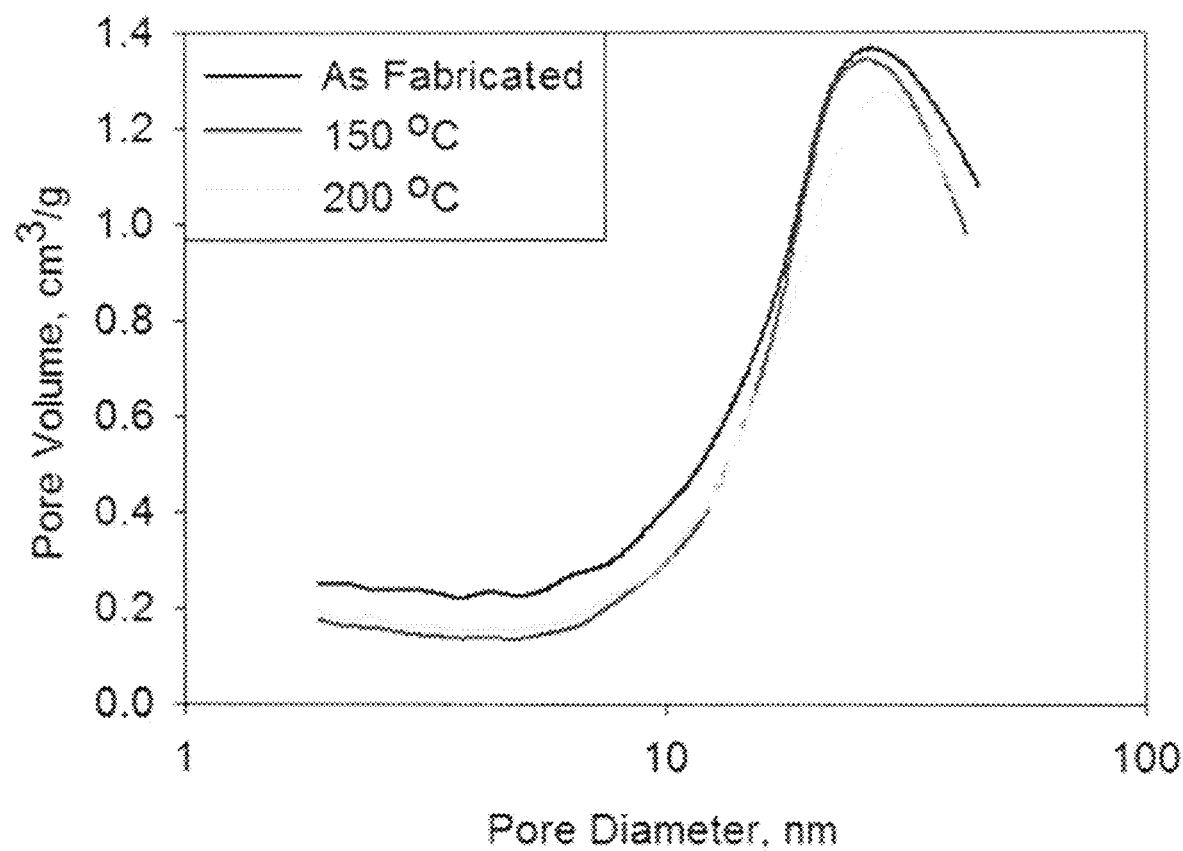
FIG. 15 is a graph depicting the comparison of the pore volume ($cm^3$/g) as a function of pore diameter (nm) for sample 18 (Table 1), containing 10 wt % polymer concentration, 50 mol % BAPF, and an n-value of 40 as fabricated, at 150° C., and at 200° C.

FIG. 15 shows the pore size distributions for representative samples (see Table 1), containing 10 wt % polymer concentration, 50% BAPF, and an n-value of 40 as fabricated, and after aging at 150° C. and at 200° C. After 150° C. aging, the largest decrease in pore volume occurs at pore sizes smaller than 10 nm, while after 200° C., the peak at about 20 nm is slightly reduced. These changes may account for the observed reductions in surface area.

Figure 4A:
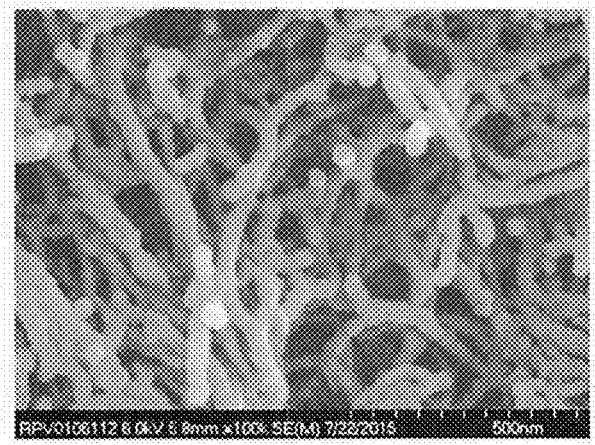
FIG. 4A and FIG. 4B are SEM images for embodiments of polyimide aerogels fabricated according to Table 1 with a polymer concentration of 7 wt %: (a) 0 mol % BAPF, n=40 (sample 14) and (b) 50 mol % BAPF, n=40 (sample 15).
Figure 4B:
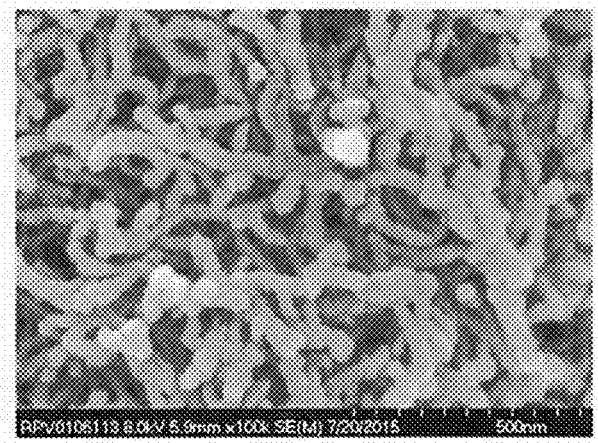
Figure 16A:
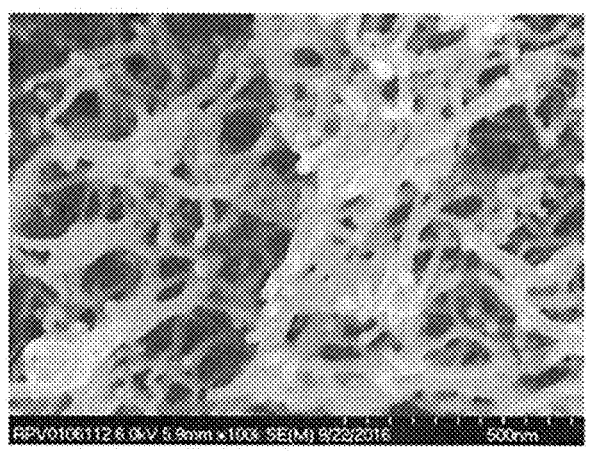
FIGS. 16A and 16B are SEM images comparing the post isothermal aging of polyimide aerogels fabricated according to embodiments of the innovation with a polymer concentration of 7 wt %: (a) 0 mol % BAPF, n=40 (sample 14 (Table 1)) and (b) 50 mol % BAPF, n=40 (sample 15 (Table 1)).
Figure 16B:
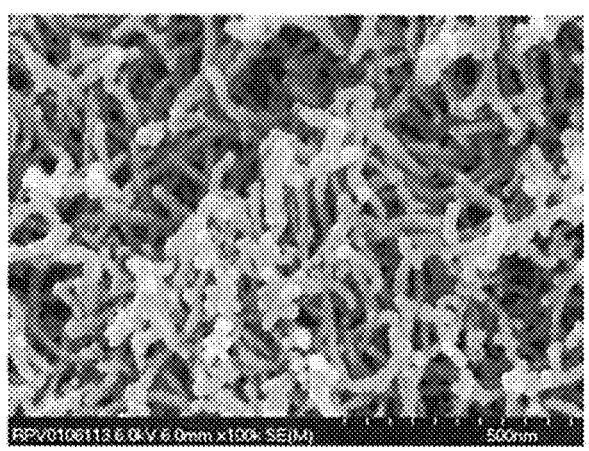

FIGS. 16A and 16B display the SEM images of samples 14 and 15, respectively, after isothermal aging at 200° C. FIGS. 4A and 4B are SEM images of the same samples prior to aging. Comparison of FIGS. 16A and 16B with FIGS. 4A and 4B shows that the samples display a degree of agglomeration of the fiber strands after aging compared to before aging. It might be expected that agglomeration and densification would be more apparent in FIG. 16A, which is the sample made with no BAPF compared to that shown in FIG. 16B made with 50 mol %, but it is difficult to see a clear difference between the two samples despite the rather pronounced difference in density. This observation is significant because the addition of diamine in the synthesis does not change the aerogel architecture which is the genesis for the aerogel's excellent insulation properties. Other methods to reduce shrinkage involve the addition of rigid-rod fillers which both increase density as well as cost and complexity due to an additional step in the synthesis.

The following examples illustrate different processes to fabricate the innovative polyimide aerogel in accordance with aspects of the innovation. It is to be understood in the following examples and in the entire disclosure, while measurements (e.g., quantity, mass, weight, volume, concentrations, heating and cooling temperatures, density, measurements of time, etc.) are disclosed, these measurements are approximate and are not intended to limit the scope of the innovation.

EXAMPLES

Materials.

Acetic anhydride (AA), triethylamine (TEA), and 1,3,5-benzenetricarbonyl trichloride (BTC) were purchased from Sigma-Aldrich (3050 Spruce Street, St. Louis, Mo. 63103) and used without further purification. Anhydrous N-methylpyrrolidone (NMP) was purchased from Tedia (1000 Tedia Way, Fairfield, Ohio 45014). 4,4'-Oxidianiline (ODA), 9,9'-bis(4-aminophenyl)fluorene (BAPF), and 3,3,'4,4'-biphenyltetracarboxylic dianhydride (BPDA) were obtained from Chriskev, Inc. (13920 W. 108th Street, Lenexa, Kans. 66215). BPDA was dried at 125° C. in vacuum for 24 h before use.

Synthesis of Polyimide Aerogels.

An array of 20 polyimide aerogels were synthesized from 3,3'4,4'-biphenyltetracarboxylic dianhydride (BPDA) and 4,4'-oxydianiline (ODA) and in some cases BPDA and a combination of ODA and 9,9'-bis(4-aminophenyl)fluorene (BAPF). The aerogels were cross-linked with 1,3,5-benzenetricarbonyl trichloride (BTC). The polymer concentration, n-value and molar concentration of ODA and BAPF were varied. The resultant aerogels were subjected to isothermal aging at 150° C. and 200° C. for up to 500 hours. Samples containing BAPF showed a reduction in thermally induced shrinkage by as much as 50% compared to unmodified polyimide aerogels.

Polyimide aerogels were fabricated according to FIG. 2 using variables provided in Table 1. For fabricating aerogels with a mixture of ODA and BAPF, the ODA was dissolved first in NMP followed by addition of all of the BPDA. This should produce a solution of mostly the n=1 oligomer, BPDA-ODABPDA, plus some excess BPDA. Addition of BAPF should produce polyamic acid oligomer with a largely alternating arrangement of BAPF-(BPDA-ODA-BPDA-BAPF).

To the polyamic acid solution was added triethylamine and acetic anhydride. Triethyl amine is a non-nucleophilic base used to abstract a proton from the amic acid intermediate facilitating ring closure to the imide. Acetic anhydride acts as a water scavenger. Once the imidized oligomers form, the cross-linker BTC, dissolved in 10 mL of NMP, is added. For samples containing only ODA and BPDA, gelation occurs in 20 min. For samples containing 50 mol % BAPF, gelation time more than doubles to 45-60 min. The increased gelation time may be due to the bulky side groups disrupting the ability for the polyimide chains to pack and increasing their solubility, or may be due to the lower reactivity of the amine compared to ODA. The variables used to synthesize the aerogels are shown in Table 1, along with density, porosity, surface area, compression properties, and the onset of decomposition for each formulation. Porosity (Π) was calculated using eq 1.

$$\Pi = 100 \times \left(1 - \frac{\rho_b}{\rho_s}\right) \quad (1)$$

where $\rho_b$ is the bulk density and $\rho_s$ is the skeletal density determined by helium pycnometry. Shrinkage given in Table 1 is the initial shrinkage as fabricated calculated based on the diameter shrinkage from the initial diameter of the cylindrical mold and diameter of aerogel post supercritical drying.

Nitrogen-adsorption porosimetry was obtained using an ASAP 2000 surface area/pore distribution analyzer (Micrometrics Instrument Corp.). Skeletal density of the specimens was determined using a Micrometrics Accupyc 1340 helium pycnometer. Thermogravimetric analysis (TGA) was carried out with a TA model 2950 HiRes instrument. Infrared spectroscopy was acquired using a Nicolet Nexus 470 FTIR spectrometer. A Bruker Avance 300 spectrometer was used to obtain solid $^{13}$C NMR spectra using cross-polarization and magic angle spinning (CP-MAS) at a rate of 11 kHz. Spectra were externally referenced to the carbonyl of glycine (176.09 ppm relative to tetramethoxysilane). Scanning electron microscopy (SEM) was used to obtain micrographs of the platinum-plated aerogels using a Hitachi S-4700 field emission microscope. Compression testing was performed following ASTM Standard D695-10.

Experimental design and analysis were conducted using Design Expert, version 9, from Stat-Ease, Inc. (Minneapolis, Minn.). A face centered, central composite design including three variables was used. The concentration of BAPF (0-50 mol % with the amount of ODA being given as 100 minus the mol % BAPF); total polymer concentration (7-10 wt %); and number of repeat units, n, in the amine end-capped oligomers (20-40) were varied. A total of 20 separate batches of aerogels were produced as summarized in Table 1, including six repeats of the center point in the design. Runs were carried out in a random order. Empirically generated data were analyzed using multiple linear regression. A full quadratic equation was developed, including all two-way interactions, for each response. Backward stepwise regression analysis was performed on the model to eliminate statistically insignificant terms (p>0.1).

Preparation of BAPF-Containing Polyimide Aerogels.

Polyimide gels were synthesized using the dianhydride BPDA; the diamines ODA and BAPF; and BTC the cross-linking agent in the polar aprotic solvent, NMP, as shown in FIG. 2. Imidization was carried out chemically at room temperature. The aerogels were formulated to have amine end-caps on the polyimide oligomers and n formulated repeat units (ranging from 20 to 40) using n equiv. of BPDA and n+1 equiv. of diamine. The oligomers were cross-linked with BTC to form gels. Table 1 outlines the variables used to prepare each sample, along with the measured properties. As an example, the procedure for the synthesis of sample 6 from Table 1 consisting of 50 mol % ODA and 50 mol % BAPF, a formulated n value of 20, and a polymer concentration of 10 wt % is as follows:

To a solution of ODA (1.906 g, 932 mmol) in 873 mL of NMP was added BPDA (5.335 g, 18.13 mmol), and the mixture was stirred for 2 h then placed in a sonic bath for 5 min to dissolve. BAPF (33172 g, 932 mmol) was then added, and the solution was further stirred until homogeneous. Afterward, acetic anhydride (13.69 mL) was added, and the mixture was stirred until it became homogeneous; this was followed by addition of TEA (233 mL). After 10 min, a solution of BTC (0.1605 g, 0.604 mmol) in 10 mL of NMP was added to the solution while stirring. Immediately after mixing, the solution was poured into syringe molds that were covered with Parafilm. The solution gelled after approximately 20 min. The gels were then aged for 24 h in the molds, after which time they were extracted into a solution of 75 v/v % NMP/25 v/v % acetone and allowed to soak overnight. Afterward, the solvent was replaced by a solution of 25 v/v % NMP/75 v/v % acetone, and the gels were allowed to soak for another 24 h, followed by four more solvent exchanges in 100% acetone in 24 h intervals. The gels were then supercritically dried using liquid $CO_2$ extraction, followed by drying under vacuum at 75° C. overnight to ensure all solvent had been removed from the samples. The resultant aerogels had a density of 0.1337 g/cm$^3$ and a porosity of 90.6%. Solid $^{13}$C NMR (ppm): 165, 143, 135, 125, 65. FTIR (δ): 1716, 1502, 1363, 1236, 1103, 1076.

What has been described above includes examples of the innovation. It is, of course, not possible to describe every conceivable composition, article, or methodology for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A polyimide aerogel comprising:
   an oligomer backbone comprising:
      a cardo-diamine comprising 9,9'-bis(4-aminophenyl) fluorene (BAPF);
      an additional diamine; and
      a dianhydride;
   wherein:
      the cardo-diamine comprises between 40 mol % and 50 mol % of the total diamine in the oligomer backbone,
      the polyimide aerogel is fabricated from a solution having a polymer concentration of between approximately 7 wt % and 10 wt %,
      a period of 500 hours of isothermal aging at 200° C. of the polyimide aerogel results in a shrinkage of the polyimide aerogel between approximately 15% and approximately 24%.

2. The polyimide aerogel of claim 1, wherein the additional diamine is selected from the group consisting of 2'-bis[4-(4-aminophenoxy)phenyl]propane (BAPP), 3,4'-oxydianiline (3,4'-ODA), 4,4'-oxydianiline (4,4'-ODA), p-p-henylene diamine (PPDA), 2,2'-dimethylbenzidine (DM-BZ), bisaniline-p-xylidene (BAX), 4,4'-bis(4-aminophenoxy)biphenyl (4,4'-BAPB), 3,3'-bis(4-aminophenoxy)biphenyl (3,3'-BAPB), 4,4'-(1,4-phenylenediisopropylidene) bisaniline (BisP), and 4,4'-(1,3-phenylenediisopropylidene) bisaniline (BisM).

3. The polyimide aerogel of claim 1, wherein a number of repeat units in the oligomer backbone is in the range of about 20 to about 40.

4. The polyimide aerogel of claim 2, wherein the dianhydride is selected from the group consisting of benzophenone-3,3',4,4'-tetracarboxylic dianhydride (BTDA), 2,2'-bis(3,4'-dicarboxyphenyl)hexafluoropropane dianhydride (6FDA), 3,3,'4,4'-biphenyltetracarboxylic dianhydride (BPDA), and pyromellitic dianhydride (PMDA), pyromellitic dianhydride (PMDA), and 4,4'-oxydiphthalic anhydride (ODPA).

5. The polyimide aerogel of claim 1, further comprising amine end caps on the oligomer backbone.

6. The polyimide aerogel of claim 1, wherein the cardodiamine comprises approximately 50 mol % of the total diamine in the oligomer backbone.

* * * * *